(12) United States Patent
Kuchimanchi et al.

(10) Patent No.: US 11,081,211 B2
(45) Date of Patent: Aug. 3, 2021

(54) METHOD AND APPARATUS FOR PROVIDING A PHARMACOKINETIC DRUG DOSING REGIMEN

(71) Applicants: BAXALTA INCORPORATED, Bannockburn, IL (US); BAXALTA GMBH, Glattpark (CH)

(72) Inventors: Kameswara Rao Kuchimanchi, Lexington, MA (US); Alexandra Loew-Baselli, Vienna (AT); Gerald Spotts, Encine, CA (US); Myungshin Oh, Los Angeles, CA (US); Michael Don Hale, Winchester, MA (US); Martin Wolfsegger, Vienna (AT)

(73) Assignees: BAXALTA INCORPORATED, Bannockburn, IL (US); BAXALTA GMBH, Glattpark (CH)

( * ) Notice: Subject to any disclaimer, the term of this patent is extended or adjusted under 35 U.S.C. 154(b) by 0 days.

(21) Appl. No.: 17/070,599

(22) Filed: Oct. 14, 2020

(65) Prior Publication Data

US 2021/0027876 A1 Jan. 28, 2021

Related U.S. Application Data

(63) Continuation of application No. 16/092,396, filed as application No. PCT/US2017/027309 on Apr. 13, (Continued)

(51) Int. Cl.
*G16H 20/17* (2018.01)
*G16H 50/70* (2018.01)
(Continued)

(52) U.S. Cl.
CPC ............ *G16C 20/30* (2019.02); *G16H 20/17* (2018.01); *G16H 50/20* (2018.01); *G16H 50/70* (2018.01);
(Continued)

(58) Field of Classification Search
None
See application file for complete search history.

(56) References Cited

U.S. PATENT DOCUMENTS

| 4,073,321 A | 2/1978 | Moskowitz |
| 4,709,331 A | 11/1987 | Barkett et al. |
| (Continued) | | |

FOREIGN PATENT DOCUMENTS

| CN | 101035579 A | 9/2007 |
| EP | 0737926 A1 | 10/1996 |
| (Continued) | | |

OTHER PUBLICATIONS

Ahnstrom, 2004, A 6-year follow-up of dosing, coagulation factor levels and bleedings in relation to joint status in the prophylactic treatment of haemophilia, Haemophilia 10:689-697.

(Continued)

*Primary Examiner* — Soren Harward
(74) *Attorney, Agent, or Firm* — Troutman Pepper Hamilton Sanders LLP

(57) ABSTRACT

Systems and methods providing a clotting factor VIII dosing regimen are disclosed. The systems and methods include determining an estimated pharmacokinetic profile of a patient using a Bayesian model of pharmacokinetic profiles of sampled patients. The systems and methods can determine a first dosing regimen for a first dosing interval including (i) a first dosage and (ii) a first therapeutic plasma protein level in the patient varying over time based at least upon the estimated pharmacokinetic profile. The systems and methods can determine a second dosing regimen for a second dosing interval including (i) a second dosage and (ii) a second therapeutic plasma protein level in the patient varying over time. The estimated pharmacokinetic profile can be adjusted based on previous patient treatments. Fur- (Continued)

ther, a user can select which days a dosage is to be applied such that the protein level does not fall below a target trough.

9 Claims, 31 Drawing Sheets

Related U.S. Application Data 2017, application No. 17/070,599, which is a continuation-in-part of application No. 14/311,113, filed on Jun. 20, 2014.

(60) Provisional application No. 61/837,421, filed on Jun. 20, 2013, provisional application No. 61/840,969, filed on Jun. 28, 2013, provisional application No. 61/881,214, filed on Sep. 23, 2013, provisional application No. 62/323,015, filed on Apr. 15, 2016.

(51) Int. Cl.
| | |
|---|---|
| *G16H 50/20* | (2018.01) |
| *G16C 20/30* | (2019.01) |
| G16C 20/50 | (2019.01) |
| G16C 20/70 | (2019.01) |
| G06N 7/00 | (2006.01) |
| G01N 33/50 | (2006.01) |
| *A61K 49/00* | (2006.01) |
| *A61P 7/04* | (2006.01) |

(52) U.S. Cl.
CPC ............ *A61K 49/0004* (2013.01); *A61P 7/04* (2018.01); *G06N 7/005* (2013.01); *G16C 20/50* (2019.02); *G16C 20/70* (2019.02)

(56) References Cited

U.S. PATENT DOCUMENTS

| | | | |
|---|---|---|---|
| 4,807,170 A | 2/1989 | Kulli et al. |
| 4,810,243 A | 3/1989 | Howson |
| 4,898,578 A | 2/1990 | Rubalcaba, Jr. |
| 5,104,374 A | 4/1992 | Bishko et al. |
| 5,318,544 A | 6/1994 | Drypen et al. |
| 5,462,222 A | 10/1995 | Boeck, II |
| 5,508,202 A | 4/1996 | Enomoto et al. |
| 5,522,798 A | 6/1996 | Johnson et al. |
| 5,526,853 A | 6/1996 | McPhee et al. |
| 5,609,575 A | 3/1997 | Larson et al. |
| 5,630,664 A | 5/1997 | Farrelly |
| 5,678,571 A | 10/1997 | Brown |
| 5,681,285 A | 10/1997 | Ford et al. |
| 5,770,384 A | 6/1998 | Androphy et al. |
| 5,789,160 A | 8/1998 | Eaton et al. |
| 5,897,493 A | 4/1999 | Brown |
| 5,915,971 A | 6/1999 | Ramsay et al. |
| 5,951,526 A | 9/1999 | Korisch et al. |
| 6,093,392 A | 7/2000 | High et al. |
| 6,099,837 A | 8/2000 | Turecek et al. |
| 6,167,412 A | 12/2000 | Simons |
| 6,188,570 B1 | 2/2001 | Borkowski |
| 6,317,719 B1 | 11/2001 | Schrier et al. |
| 6,321,164 B1 | 11/2001 | Braun et al. |
| 6,330,426 B2 | 12/2001 | Brown et al. |
| 6,381,577 B1 | 4/2002 | Brown |
| 6,421,650 B1 | 7/2002 | Goetz et al. |
| 6,489,289 B2 | 12/2002 | Nortersheuser et al. |
| 6,542,858 B1 | 4/2003 | Grass et al. |
| 6,564,153 B2 | 5/2003 | Braun et al. |
| 6,647,358 B2 | 11/2003 | Grass et al. |
| 6,658,396 B1 | 12/2003 | Tang et al. |
| 6,747,002 B2 | 6/2004 | Cheung et al. |
| 6,790,668 B1 | 9/2004 | Ferreira et al. |
| 6,944,638 B1 | 9/2005 | Putnam |
| 6,978,286 B2 | 12/2005 | Francis et al. |
| 7,043,415 B1 | 5/2006 | Dunlavey et al. |
| 7,204,823 B2 | 4/2007 | Estes et al. |
| 7,229,430 B2 | 6/2007 | Hickle et al. |
| 7,693,697 B2 | 4/2010 | Westenskow et al. |
| 7,813,880 B2 | 10/2010 | Vaidya et al. |
| 7,837,647 B2 | 11/2010 | Estes et al. |
| 7,860,583 B2 | 12/2010 | Condurso et al. |
| 7,862,506 B2 | 1/2011 | Brown |
| 7,867,165 B2 | 1/2011 | Brown |
| 7,869,852 B2 | 1/2011 | Brown |
| 7,871,376 B2 | 1/2011 | Brown |
| 7,875,288 B2 | 1/2011 | Balu-Iyer et al. |
| 7,972,267 B2 | 7/2011 | Brown |
| 7,990,251 B1 | 8/2011 | Ford, Jr. |
| 7,997,269 B2 | 8/2011 | Yudkovitch et al. |
| 7,998,734 B2 | 8/2011 | High et al. |
| 8,156,158 B2 | 4/2012 | Rolls et al. |
| 8,326,545 B2 | 12/2012 | Yudkovitch et al. |
| 8,326,649 B2 | 12/2012 | Rosenfeld |
| 8,412,538 B2 | 4/2013 | Hardaway |
| 8,449,884 B2 | 5/2013 | Rivera et al. |
| 8,512,309 B2 | 8/2013 | Shemesh et al. |
| 8,540,664 B2 | 9/2013 | Robertson et al. |
| 8,546,096 B2 | 10/2013 | Dockal et al. |
| 8,574,856 B2 | 11/2013 | Selinfreund et al. |
| 8,589,175 B2 | 11/2013 | Glauser et al. |
| 8,589,186 B1 | 11/2013 | Nadas et al. |
| 8,606,526 B1 | 12/2013 | Fernandez et al. |
| 8,616,895 B2 | 12/2013 | Brown |
| 8,630,722 B2 | 1/2014 | Condurso et al. |
| 8,637,320 B2 | 1/2014 | Schubert et al. |
| 8,644,754 B2 | 2/2014 | Brown |
| 8,655,259 B2 | 2/2014 | Brown et al. |
| 8,679,014 B2 | 3/2014 | Bennett et al. |
| 8,682,687 B2 | 3/2014 | Hyde et al. |
| 8,744,828 B2 | 6/2014 | Albisser et al. |
| 8,761,906 B2 | 6/2014 | Condurso et al. |
| 8,969,524 B2 | 3/2015 | Steinitz et al. |
| 9,050,318 B2 | 6/2015 | Dumont et al. |
| 9,061,038 B2 | 6/2015 | Garland et al. |
| 9,119,918 B2 | 9/2015 | Robertson et al. |
| 9,142,144 B2 | 9/2015 | Meglan et al. |
| 9,241,978 B2 | 1/2016 | Dumont et al. |
| 9,249,209 B2 | 2/2016 | Cho et al. |
| 9,272,021 B2 | 3/2016 | Scheiflinger et al. |
| 9,307,907 B2 | 4/2016 | Condurso et al. |
| 9,340,792 B2 | 5/2016 | Klaenhammer et al. |
| 9,358,361 B2 | 6/2016 | Hyde et al. |
| 9,398,863 B2 | 7/2016 | Viertio-Oja |
| 9,452,108 B2 | 9/2016 | Ariagno et al. |
| 9,500,639 B2 | 11/2016 | Dayel et al. |
| 9,512,198 B2 | 12/2016 | Steinitz et al. |
| 9,572,511 B2 | 2/2017 | Kochba et al. |
| 9,585,671 B2 | 3/2017 | Hen et al. |
| 9,603,860 B2 | 3/2017 | Perrin et al. |
| 2001/0001144 A1 | 5/2001 | Kapp |
| 2001/0041964 A1 | 11/2001 | Grass et al. |
| 2002/0010595 A1 | 1/2002 | Kapp |
| 2002/0019706 A1 | 2/2002 | Braun et al. |
| 2002/0130779 A1 | 9/2002 | Ford |
| 2003/0023461 A1 | 1/2003 | Quintanilla et al. |
| 2003/0050225 A1 | 3/2003 | Butenas et al. |
| 2003/0051737 A1 | 3/2003 | Hickle et al. |
| 2003/0078760 A1 | 4/2003 | Bachman et al. |
| 2004/0023211 A1 | 2/2004 | Groen et al. |
| 2004/0193019 A1 | 9/2004 | Wei |
| 2005/0008580 A1 | 1/2005 | Gong et al. |
| 2005/0054942 A1 | 3/2005 | Melker et al. |
| 2005/0075627 A1 | 4/2005 | Ward |
| 2005/0130236 A1 | 6/2005 | Goldman |
| 2005/0147618 A1 | 7/2005 | Rivera et al. |
| 2005/0165221 A1 | 7/2005 | Booth et al. |
| 2005/0215957 A1 | 9/2005 | Hynes |
| 2006/0015261 A1 | 1/2006 | Mann et al. |
| 2006/0047538 A1 | 3/2006 | Condurso et al. |
| 2006/0078897 A1 | 4/2006 | Wedinger et al. |
| 2006/0128624 A1 | 6/2006 | Cheung et al. |
| 2006/0129357 A1 | 6/2006 | Francis et al. |
| 2006/0161408 A1 | 7/2006 | Bachman et al. |

(56) References Cited

U.S. PATENT DOCUMENTS

| | | |
|---|---|---|
| 2006/0271405 A1 | 11/2006 | Cipolle et al. |
| 2007/0061393 A1 | 3/2007 | Moore |
| 2007/0067148 A1 | 3/2007 | Fritzson et al. |
| 2007/0106536 A1 | 5/2007 | Moore |
| 2007/0106750 A1 | 5/2007 | Moore |
| 2007/0106753 A1 | 5/2007 | Moore |
| 2007/0167853 A1 | 7/2007 | Melker et al. |
| 2007/0196479 A1 | 8/2007 | Willmann et al. |
| 2008/0008991 A1 | 1/2008 | Groen et al. |
| 2008/0033661 A1 | 2/2008 | Syroid et al. |
| 2008/0040151 A1 | 2/2008 | Moore |
| 2008/0051460 A1 | 2/2008 | Hobden et al. |
| 2008/0052317 A1 | 2/2008 | Francis et al. |
| 2008/0091083 A1 | 4/2008 | Yudkovitch et al. |
| 2008/0091084 A1 | 4/2008 | Yudkovitch et al. |
| 2008/0103824 A1 | 5/2008 | Francis et al. |
| 2008/0108942 A1 | 5/2008 | Brister et al. |
| 2008/0213222 A1 | 9/2008 | High et al. |
| 2009/0006061 A1 | 1/2009 | Thukral et al. |
| 2009/0006133 A1 | 1/2009 | Weinert et al. |
| 2009/0144082 A1 | 6/2009 | Selbst et al. |
| 2009/0144089 A1 | 6/2009 | Heywood et al. |
| 2009/0306944 A1 | 12/2009 | Willmann et al. |
| 2009/0327175 A1 | 12/2009 | He et al. |
| 2010/0036676 A1 | 2/2010 | Safdi et al. |
| 2010/0121185 A1 | 5/2010 | Hyde et al. |
| 2010/0124536 A1 | 5/2010 | Schaub et al. |
| 2010/0143326 A1 | 6/2010 | Rischel et al. |
| 2010/0152545 A1 | 6/2010 | Ramsay et al. |
| 2010/0152620 A1 | 6/2010 | Ramsay et al. |
| 2010/0169063 A1 | 7/2010 | Yudkovitch et al. |
| 2010/0205001 A1 | 8/2010 | Knudsen et al. |
| 2010/0273738 A1 | 10/2010 | Valcke et al. |
| 2010/0312578 A1 | 12/2010 | Hardaway |
| 2011/0015939 A1 | 1/2011 | Lara Gonzalez |
| 2011/0040481 A1 | 2/2011 | Trombley et al. |
| 2011/0060578 A1 | 3/2011 | Ward et al. |
| 2011/0077963 A1 | 3/2011 | Knudsen et al. |
| 2011/0110921 A1 | 5/2011 | Dockal et al. |
| 2011/0145936 A1 | 6/2011 | Ostertag et al. |
| 2011/0184379 A1 | 7/2011 | Van Antwerp et al. |
| 2011/0263690 A1 | 10/2011 | High et al. |
| 2011/0295341 A1 | 12/2011 | Estes et al. |
| 2012/0022497 A1 | 1/2012 | Brown |
| 2012/0041414 A1 | 2/2012 | Estes et al. |
| 2012/0041415 A1 | 2/2012 | Estes et al. |
| 2012/0045742 A1 | 2/2012 | Meglan et al. |
| 2012/0158424 A1 | 6/2012 | Knudsen et al. |
| 2012/0232517 A1 | 9/2012 | Saiki |
| 2012/0316116 A1 | 12/2012 | Scheiflinger et al. |
| 2013/0085712 A1 | 4/2013 | Wang et al. |
| 2013/0085772 A1 | 4/2013 | Gaweda et al. |
| 2013/0108629 A1 | 5/2013 | Dumont et al. |
| 2013/0273047 A1 | 10/2013 | Rivera et al. |
| 2013/0296823 A1 | 11/2013 | Melker et al. |
| 2014/0005501 A1 | 1/2014 | Schabbach et al. |
| 2014/0050717 A1 | 2/2014 | Dockal et al. |
| 2014/0100829 A1 | 4/2014 | Mould |
| 2014/0114676 A1 | 4/2014 | Holmes |
| 2014/0261860 A1 | 9/2014 | Heath et al. |
| 2014/0303901 A1 | 10/2014 | Sadeh |
| 2014/0379629 A1 | 12/2014 | Loew-Baselli et al. |
| 2015/0032470 A1 | 1/2015 | Knudsen et al. |
| 2015/0044207 A1 | 2/2015 | Rivera et al. |
| 2015/0052623 A1 | 2/2015 | Crawford |
| 2015/0053711 A1 | 2/2015 | Ariagno et al. |
| 2015/0185235 A1 | 7/2015 | Sommer |
| 2015/0266944 A1 | 9/2015 | Jiang et al. |
| 2015/0356252 A1 | 12/2015 | Beker |
| 2016/0033523 A1 | 2/2016 | Cameron et al. |
| 2016/0151015 A1 | 6/2016 | Condurso et al. |
| 2016/0174534 A1 | 6/2016 | Ostertag et al. |
| 2016/0184403 A1 | 6/2016 | Scheiflinger et al. |
| 2016/0210436 A1 | 7/2016 | Ambrose et al. |
| 2016/0296607 A1 | 10/2016 | Jiang |
| 2016/0300037 A1 | 10/2016 | Mould |
| 2016/0306945 A1 | 10/2016 | Jiang |
| 2016/0335473 A1 | 11/2016 | Pamelard et al. |
| 2016/0346365 A1 | 12/2016 | Pierce et al. |

FOREIGN PATENT DOCUMENTS

| | | |
|---|---|---|
| JP | 2006-155071 A | 6/2006 |
| JP | 2008-516303 A | 5/2008 |
| JP | 2012-135439 A | 7/2012 |
| JP | 2013-512678 A | 4/2013 |
| KR | 20-0166416 Y1 | 2/2000 |
| WO | 00/15178 A2 | 3/2000 |
| WO | 2002/023186 A2 | 3/2002 |
| WO | 2004/070994 A1 | 8/2004 |
| WO | 2005/038049 A2 | 4/2005 |
| WO | 2012/079576 A1 | 6/2012 |
| WO | 2012/160161 A1 | 11/2012 |
| WO | 2012/166795 A1 | 12/2012 |
| WO | 2014/003614 A1 | 1/2014 |
| WO | 2014/041529 A1 | 3/2014 |
| WO | 2014/063108 A1 | 4/2014 |
| WO | 2014/070953 A1 | 5/2014 |
| WO | 2015/006033 A1 | 1/2015 |
| WO | 2017/180807 A1 | 10/2017 |

OTHER PUBLICATIONS

Bjorkman, 2003, Prophylactic dosing of factor VIII and factor IX from a clinical pharmacokinetic perspective, Haemophilia 9(Suppl 1):101-108.

Bjorkman, 2010, Limited blood sampling for pharmacokinetic dose tailoring of FVIII in the prophylactic treatment of haemophilia A, Haemophilia 16:597-605.

Bjorkman, 2012, Population pharmacokinetics of recombinant factor VIII: the relationships of pharmacokinetics to age and body weight, Blood 119(2):612-618.

Carlsson, 1993, Pharmacokinetic dosing in prophylactic treatment of hemophilia A, Eur J Haematology 51(4):247-52.

Collins, 2010, Factor VIII requirement to maintain a target plasma level in the prophylactic treatment of severe hemophilia A: Influences of variance in pharmacokinetics and treatment regimens, J Thrombosis and Haemostasis 8:269-275.

Collins, 2011, Implications of coagulation factor VIII and IX pharmacokinetics in the prophylactic treatment of haemophilia, Haemophilia 17:2-10.

Duffull, 1997, Comparison of two Bayesian approaches to dose-individualization for once-daily aminoglycoside regimens, B J Clin Pharmacol 43(2):125-35.

International Search Report and Written Opinion dated Jul. 17, 2017, for PCT/US2017/027309, filed Apr. 13, 2017 (10 pages).

Jelliffe, 1993, Individualizing drug dosage regimens: roles of population pharmacokinetic and dynamic models, Bayesian fitting, and adaptive control, Therapeutic Drug Monitoring 15:380-393.

Ljung, 2009, Prophylactic therapy in haemophilia, Blood Reviews 23:267-274.

Lunn, 2005, Bayesian Analysis of Population Pharmacokinetic/Pharmacodynamic Models. in Probabilistic Modeling in Bioinformatics and Medical Informatics, Husmeier et al., Eds. pp. 351-370 (London).

McMichael, 1993, An intelligent and cost-effective computer dosing system for individualizing FK506 therapy in transplantation and autoimmune disorders, J Clin Pharmacol 33:599-605.

Mondorf, 2009, Haemoassist-a hand-held electronic patient diary for haemophilia home care, Haemophilia 15:464-472.

Sherif, 2015, Protocols for secure electronic commerce, 3rd Ed., Taylor & Francis Group, Boca Raton FL 33487 (444 pages).

Björkman, S., et al., "Pharmacokinetics and dose requirements of factor VIII over the age ranges 3-74 years" Eur J. Clin Pharmacol 65:989-998 (2009).

Lanao, J., M., et al., "Pharmacokinetic basis for the use of extended interval dosage regimens of gentamicin in neonates" Journal of Antimicrobial Chemotherapy 54:193-198 (2004).

(56) References Cited

OTHER PUBLICATIONS

Extended European Search Report issued in corresponding European Patent Application No. 17783092.4 dated Jun. 8, 2020.
Search Report issued in corresponding Georgian Patent Application No. AP 2017 14920 dated Feb. 25, 2020, with informal translation.
Notification of Deficiencies issued in corresponding Israeli Patent Application No. 262226 dated Apr. 23, 2020, with informal translation.
Kelman et al., OPT: A Package of Computer Programs for Parameter Optimisation in Clinical Pharmacokinetics, Br. J. Clin. Pharmac. (1982), 14, 247-256.

FIG. 3

Login

First Name *
Last Name *
Specialty *
Hospital Name
Address *
City *
State *  IL
Zip Code *
Country *  United States Email *
Repeat Email *
Day Time Phone
Mobile Number
Fax Number
How did you hear about us?  Newspaper
DEA Number *

☐ I confirm that my DEA Number may be used to verify my identity and I am a registered Healthcare Professional *

SAMPLES

Washout: Yes | No

Pre-infusion FVIII level (IU/dL): [ ]

| PK Assessment | Sample | Last Edit | Collection Date & Time | Hours After | FVIII Level (IU/dL) | Assay Type | | |
|---|---|---|---|---|---|---|---|---|
| 1 | 1 | 08-May-2014 01:47 | 06-May-2014 16:00 | 6.00 | 57.0 | One-Stage | Included | Excluded |
| 1 | 2 | 08-May-2014 01:47 | 07-May-2014 10:00 | 24.00 | 15.0 | One-Stage | Included | Excluded |
| 1 | 3 | 08-May-2014 01:47 | 07-May-2014 16:00 | 30.00 | 10.0 | One-Stage | Included | Excluded |

Add Sample

Reminder: PK profiles should only be generated using the same assay type.

| | Bayesian Estimate |
|---|---|
| Clearance (dL/hr/kg) | 0.035 |
| Volume in steady state (dL/kg) | 0.5 |
| FVIII half-life (hours) | 11.8 |
| Time to 1% above baseline (hours) | 70.0 |

Next Step

FIG. 6

| General Patient Information | | | | | | |
|---|---|---|---|---|---|---|
| Patient History | | | | | | |
| Calculation | | | | | | |
| Visit# | Sample# | Collection Date/Time | Observed IU/dl | Theoretical IU/dl | Adjusted IU/dl | |
| A123-001 | 01 | 20-12-2011 8:00am | 5 | 4.86 | 4.66 | ✏ ON |
| A123-002 | 01 | 01-08-2012 8:00am | 5 | 4.86 | 4.66 | ✏ ON |
| A123-002 | 02 | 05-08-2012 8:00am | 5 | 4.83 | 4.50 | ✏ ON |

Add sample

| | Theoretical | Adjusted | Offset |
|---|---|---|---|
| Clearance (L/hr) | | | |
| vdBeta | | | |
| cMax / Peak (IU/dL) | | | |
| FVIII half-life (hours) | | | |
| Time to 1% (hours) | | | |

Calculate  Next Step

Dosage

Visit History

| Visit# | Sample# | Collectoin Date/Time | Observed IU/dL | Theoretical IU/dL | Adjusted IU/dL | | |
|---|---|---|---|---|---|---|---|
| A123-001 | 01 | 20-12-2011 8:00am | 5 | 4.86 | 4.66 | ✏ | ON |
| A123-002 | 01 | 01-08-2012 8:00am | 5 | 4.86 | 4.66 | ✏ | ON |
| A123-002 | 02 | 05-08-2012 8:00am | 5 | 4.83 | 4.50 | ✏ | OFF |
| A123-004 | 01 | 05-08-2012 8:00am | 10 | 9.86 | 9.66 | ✏ | ON |

Add sample

| | Theoretical | Adjusted | Offset |
|---|---|---|---|
| Clearance (L/hr) | 0.68 | 0.67 | 0.01 |
| vdBeta | 11.86 | 11.86 | 0 |
| cMax / Peak (IU/dL) | 20.65 | 16.86 | 3.79 |
| FVIII half-life (hours) | 12.07 | 12.18 | -0.11 |
| Time to 1% (hours) | 1.93 | 1.82 | 0.11 |

Calculate

Next Step

FIG. 8

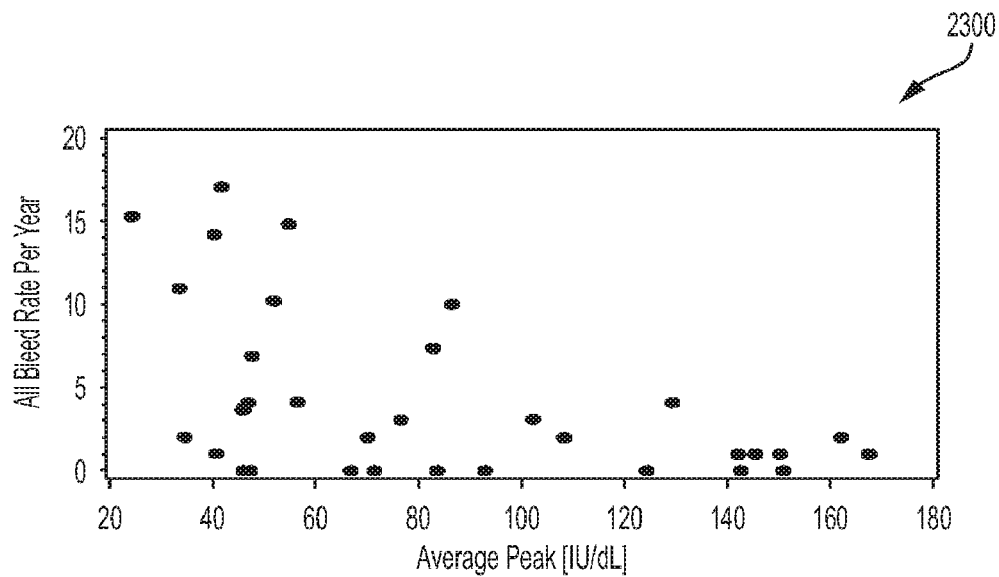
FIG. 23
FIG. 24
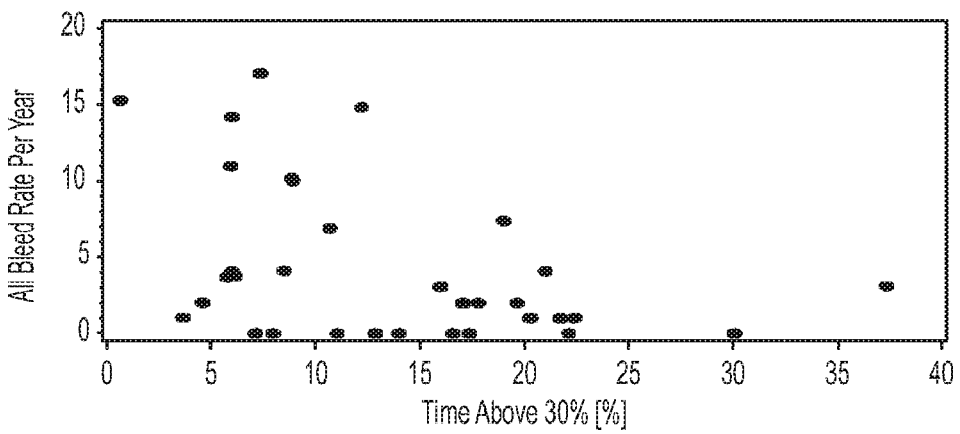
FIG. 25

| | All Bleeding | | Joint Bleeding | |
|---|---|---|---|---|
| | Coeff. | P-value | Coeff. | P-value |
| Time Spent> 10%* | | NS | | NS |
| Time Spent> 20% | | NS | -0.0578 | S |
| Time Spent> 30% | -0.0786 | S | -0.0832 | S |
| Time Spent> 40% | -0.0911 | S | -0.0951 | S |

|  | All Bleeding | | Joint Bleeding | |
|---|---|---|---|---|
|  | Coeff. | P-value | Coeff. | P-value |
| Log₁₀(Weekly AUC> 5%) | -3.1307 | S | -3.0986 | S |
| Log₁₀(Weekly AUC> 10%) | -2.6189 | S | -2.5856 | S |
| Log₁₀(Weekly AUC> 20%) | -1.9820 | S | -1.9474 | S |

FIG. 28

| Variable | Time>05% <br> Time>10% <br> Time>20% | AUC>05% <br> AUC>10% <br> AUC>20% |
|---|---|---|
| Average Cmax | 0.15 (ns) <br> 0.43 (ns) <br> 0.65 (s) | 0.82 (s) <br> 0.82 (s) <br> 0.87 (s) |
| Time>05% <br> Time>10% <br> Time>20% |  | 0.60 (s) <br> 0.81 (s) <br> 0.90 (s) |

FIG. 29

METHOD AND APPARATUS FOR PROVIDING A PHARMACOKINETIC DRUG DOSING REGIMEN

PRIORITY CLAIM

The present application is a continuation of, and claims priority under 35 U.S.C. § 120 to, U.S. patent application Ser. No. 16/092,396, filed Oct. 9, 2018, which is a national stage entry of International Application No. PCT/US2017/027309, having an international filing date of Apr. 13, 2017, which claims the benefit of U.S. Provisional Patent Application No. 62/323,015, filed Apr. 15, 2016, and the present application is a continuation-in-part of, and claims priority under 35 U.S.C. § 120 to, U.S. patent application Ser. No. 14/311,113, filed Jun. 20, 2014, which claims priority to and the benefit of U.S. Provisional Patent Application No. 61/837,421, filed Jun. 20, 2013, U.S. Provisional Patent Application No. 61/840,969, filed Jun. 28, 2013, and U.S. Provisional Patent Application No. 61/881,214, filed Sep. 23, 2013. The entire contents of these applications are herein incorporated by reference as if fully set forth below.

BACKGROUND

Clotting factor VIII is a blood-clotting protein that is activated in response to an injury or bleed. Individuals with relatively low levels of clotting factor VIII are susceptible to internal or external episodes of prolonged bleeding resulting from an injury and/or spontaneous bleeding without a cause. While skin bleeds are not serious, internal bleeding of joints, muscles, and organs can cause permanent damage, disfigurement, or even death.

Patients with hemophilia A have a genetic deficiency that causes low levels of clotting factor VIII. The amount of clotting factor VIII in a patient is expressed as a percentage relative to a normal level. Patients with 5 to 40% of clotting factor VIII are considered to have a mild form of hemophilia A while patients with 1 to 5% of clotting factor VIII are considered to have a moderate form of hemophilia A. Patients with less than 1% of clotting factor VIII are considered to have a severe form of hemophilia A.

Treatment of patients with hemophilia A (or patients that otherwise have low levels of clotting factor VIII) includes providing these patients with periodic infusions of a clotting factor concentrate (e.g., therapeutic plasma protein). The clotting factor concentrate acts as a replacement or supplement for the patient's natural occurring clotting factor VIII. One example of such a therapeutic plasma protein is Shire's ADVATE drug. In some instances, patients receive the therapeutic plasma protein in response to having an uncontrolled internal bleed. Alternatively, patients may be prescribed a prophylactic treatment regimen of the therapeutic plasma protein to reduce the possibility of future bleeds. Oftentimes, this regimen requires that a patient visit a healthcare provider and/or self-infuse the therapeutic plasma protein three or more times a week to receive treatments.

The goal of a treatment regimen is to schedule patient visits such that the clotting factor VIII, as provided by the therapeutic plasma protein, does not fall below a predetermined threshold, such as one percent (1%). However, the amount of therapeutic plasma protein needed in a patient is dependent upon the dosing amount and metabolism of the clotting factor VIII by the patient. Additionally, because there is a wide variability in the clotting factor VIII pharmacokinetic disposition in the population, many patients may not be dosed properly to maintain the intended FVIII target trough across the dosing interval. Thus, it is necessary to determine the individual patient's pharmacokinetic profile to ensure the proper dose is administered for the chosen time interval.

To prescribe a treatment regimen, currently a healthcare provider determines how an administered dose of a therapeutic plasma protein is eliminated from a patient over a treatment time to identify a pharmacokinetic profile of the patient. Oftentimes the determination of a patient's full pharmacokinetic profile requires ten or more blood draws to determine a level or concentration of the therapeutic plasma protein within the patient at different times from initial administration of the therapeutic plasma protein dose (e.g., determine how the therapeutic plasma protein is eliminated over time). These multiple blood draws require a patient to stay within a healthcare facility for a prolonged duration or visit the healthcare facility multiple times. These multiple visits and/or multiple blood draws place considerable stress on the patient and the healthcare facility.

To avoid any chance of a patient falling below a predetermined threshold, many healthcare providers design treatment regimens that require patients to receive a therapeutic plasma protein infusion every one, two, or three days in accordance with an approved product label. An every-one-day or every-two-day regimen places stress on patients by requiring them to infuse relatively frequently. The every-one-day and every-two-day regimens may also be unnecessary for some patients. However, the every-one-day and every-two-day regimens make it easier and more practical for a healthcare provider to maintain higher therapeutic plasma protein levels in a patient above a specified peak therapeutic plasma protein level.

SUMMARY

An example system, method, and apparatus are disclosed that determine a therapeutic plasma protein dosing regimen for a patient. The example system, method, and apparatus determine the dosing regimen using a pharmacokinetic profile of the patient that is derived from a pharmacokinetic model of a previously sampled patient population and/or individual patient information. The pharmacokinetic profile of the patient may be refined or modified based on previous therapeutic plasma protein treatments of the patient and/or patient specific characteristics such as age, body weight, other plasma protein levels, physical activity level, gender, disease state, etc. The system, method, and apparatus provide a graphical interface of the pharmacokinetic profile of the patient that enables a user (e.g., a health care professional) to adjust dosage, dosing interval, and a minimum acceptable concentration of the therapeutic plasma protein within the patient to view how the dosing regimen changes. Such a configuration enables a healthcare provider to determine an optimal dosing regimen that reduces (or prevents) a patient from risk of bleeds as a result of having low levels of clotting factor VIII.

In an example embodiment, a method includes determining an estimated pharmacokinetic profile of a patient using a Bayesian model of pharmacokinetic profiles of sampled patients, the estimated pharmacokinetic profile based upon at least one of a body weight or an age of the patient. The example method also includes determining a first dosing regimen for a first specified dosing interval including (i) a first dosage and (ii) a first therapeutic plasma protein level in the patient over a time period based at least upon the estimated pharmacokinetic profile and determining a second dosing regimen for a second specified dosing interval including (i) a second dosage and (ii) a second therapeutic plasma protein level in the patient over the time period based at least upon the estimated pharmacokinetic profile. The method further includes displaying the first dosing regimen and the second dosing regimen on a client device such that the first dosing regimen is displayed in conjunction with the second dosing regimen.

In another example embodiment, an apparatus includes a model generator configured to create a Bayesian model of pharmacokinetic profiles of sampled patients, the Bayesian model including a (i) therapeutic plasma protein clearance and (ii) a volume of distribution relationship for a therapeutic plasma protein based upon at least one of patient age or body weight. The example apparatus also includes a pharmacokinetic server configured to determine an approximate pharmacokinetic profile of a patient based upon the Bayesian model and at least one of an age of the patient or a body weight of the patient and determine a therapeutic plasma protein dosing regimen including a dosage and a therapeutic plasma protein level over a time period based upon the approximate pharmacokinetic profile of the patient. The pharmacokinetic server is also configured to modify the therapeutic plasma protein dosing regimen in response to receiving a dosing interval for applying the dosage to the patient and transmit the modified therapeutic plasma protein dosing regimen to a client device.

In yet another example embodiment, a machine-accessible device has instructions stored thereon that are configured, when executed, to cause a machine to at least prompt a user to enter at least one of a patient body weight or age and use a Bayesian model of pharmacokinetic profiles of sampled patients to determine an approximate pharmacokinetic profile of a patient based upon the Bayesian model and the at least one of entered patient body weight or age, the Bayesian model including (i) a therapeutic plasma protein clearance and (ii) a volume of distribution relationship for a therapeutic plasma protein based upon the at least one of entered patient body weight or age. The example instructions also cause the machine to determine a dosing regimen for the patient based upon the approximate pharmacokinetic profile of the patient, the dosing regimen including a dosage and a dosage interval. The example instructions further cause the machine to modify the dosing regimen in response to receiving another dosing interval for applying the dosage to the patient and enable the dosing regimen and a time-varying therapeutic plasma protein level based on the dosing regimen to be displayed to a user.

Aspects of the subject matter described herein may be useful alone or in combination with one or more other aspect described herein. Without limiting the foregoing description, in a first aspect of the present disclosure, a method for providing a therapeutic plasma protein dosing regimen includes determining, via a processor, an estimated pharmacokinetic profile of a patient using a Bayesian model of pharmacokinetic profiles of sampled patients, the estimated pharmacokinetic profile based upon at least one of a body weight or an age of the patient, determining, via the processor, a first dosing regimen for a first specified dosing interval including (i) a first dosage and (ii) a first therapeutic plasma protein level in the patient over a time period based at least upon the pharmacokinetic profile, determining, via the processor, a second dosing regimen for a second specified dosing interval including (i) a second dosage and (ii) a second therapeutic plasma protein level in the patient over the time period based at least upon the pharmacokinetic profile, and displaying the first dosing regimen and the second dosing regimen on a client device such that the first dosing regimen is displayed in conjunction with the second dosing regimen.

In accordance with a second aspect of the present disclosure, which may be used in combination with the first aspect, the method further includes adjusting, via the processor, the estimated pharmacokinetic profile of the patient based upon previous treatments of the patient.

In accordance with a third aspect of the present disclosure, which may be used in combination with any one or more of the preceding aspects, the second specified dosing interval is longer than the first specified dosing interval.

In accordance with a fourth aspect of the present disclosure, which may be used in combination with any one or more of the preceding aspects, the first specified dosing interval is 48 hours and the second specified dosing interval is 72 hours.

In accordance with a fifth aspect of the present disclosure, which may be used in combination with any one or more of the preceding aspects, the minimum threshold level is less than 20%.

In accordance with a sixth aspect of the present disclosure, which may be used in combination with any one or more of the preceding aspects, the first dosage is determined such that the first therapeutic plasma protein level in the patient over the time period does not fall below the minimum threshold level.

In accordance with a seventh aspect of the present disclosure, which may be used in combination with any one or more of the preceding aspects, the first therapeutic plasma protein level in the patient is based upon at least one of a minimum threshold level, the first dosage, or the first specified dosing interval, and the second therapeutic plasma protein level in the patient is based upon at least one of the minimum threshold level, the second dosage, or the second specified dosing interval.

In accordance with an eighth aspect of the present disclosure, which may be used in combination with any one or more of the preceding aspects, the Bayesian model includes a two-compartment model having a first compartment corresponding to a time to metabolize the therapeutic plasma protein and a second compartment corresponding to a dose for achieving a certain amount of the therapeutic plasma protein within the patient. In some embodiments, the Bayesian model may mathematically describe a pharmacokinetic disposition of clotting factor FVIII once administered to a patient.

In accordance with a ninth aspect of the present disclosure, which may be used in combination with any one or more of the preceding aspects, an apparatus for providing a therapeutic plasma protein dosing regimen to a client device includes a model generator configured to create a Bayesian model of pharmacokinetic profiles of sampled patients, the Bayesian model including a (i) therapeutic plasma protein clearance and (ii) a volume of distribution relationship for a therapeutic plasma protein based upon at least one of patient age or body weight and a pharmacokinetic server configured to determine an approximate pharmacokinetic profile of a patient based upon the Bayesian model and at least one of an age of the patient or a body weight of the patient, determine the therapeutic plasma protein dosing regimen including a dosage and a therapeutic plasma protein level over a time period based upon the approximate pharmacokinetic profile of the patient, modify the therapeutic plasma protein dosing regimen in response to receiving a dosing interval for applying the dosage to the patient, and transmit the modified therapeutic plasma protein dosing regimen to the client device.

In accordance with a tenth aspect of the present disclosure, which may be used in combination with any one or more of the preceding aspects, the dosing interval is a two-day dosing interval, and wherein the pharmacokinetic server is configured to further modify the therapeutic plasma protein dosing regimen in response to receiving a three-day dosing interval in place of the two-day dosing interval.

In accordance with an eleventh aspect of the present disclosure, which may be used in combination with any one or more of the preceding aspects, the pharmacokinetic server is configured to transmit a drug dosing tool to the client device, the drug dosing tool being configured to determine the therapeutic plasma protein dosing regimen and the modified therapeutic plasma protein dosing regimen.

In accordance with a twelfth aspect of the present disclosure, which may be used in combination with any one or more of the preceding aspects, the pharmacokinetic server is further configured to modify the therapeutic plasma protein dosing regimen based on daily activities of the patient.

In accordance with a thirteenth aspect of the present disclosure, which may be used in combination with any one or more of the preceding aspects, the pharmacokinetic server is further configured to transmit the modified therapeutic plasma protein dosing regimen to an infusion pump for administering the therapeutic plasma protein to the patient. In this aspect and any other aspect, a physician, via the pharmacokinetic server, can locally or remotely control the infusion pump such that the patient is only dosed (i.e., administered) with an amount of the therapeutic plasma protein that is consistent with a current dosing regimen based on the pharmacokinetic profile of the patient. Additionally, the physician, via the drug dosing tool, can remotely monitor and provide the patient with a renewed prescription of the therapeutic plasma protein based on a currently an available quantity of the therapeutic.

In accordance with a fourteenth aspect of the present disclosure, which may be used in combination with any one or more of the preceding aspects, the approximate pharmacokinetic profile is a first approximate pharmacokinetic profile determined for a first therapeutic plasma protein treatment of the patient, and wherein the pharmacokinetic server is further configured to determine a second approximate pharmacokinetic profile for the patient for a second therapeutic plasma protein treatment of the patient based on the modified therapeutic plasma protein dosing regimen.

In accordance with a fifteenth aspect of the present disclosure, which may be used in combination with any one or more of the preceding aspects, the volume of distribution relationship for the therapeutic plasma protein is a relationship for at least one of clotting factor VIII and modified forms of clotting factor VIII.

In accordance with a sixteenth aspect of the present disclosure, which may be used in combination with any one or more of the preceding aspects, a machine-accessible device has instructions stored thereon that are configured, when executed, to cause a machine to at least prompt a user to enter at least one of a patient body weight or age, use a Bayesian model of pharmacokinetic profiles of sampled patients to determine an approximate pharmacokinetic profile of a patient based upon the Bayesian model and the at least one of entered patient body weight or age, the Bayesian model including (i) a therapeutic plasma protein clearance and (ii) a volume of distribution relationship for a therapeutic plasma protein based upon the at least one of entered patient body weight or age, determine a dosing regimen for the patient based upon the approximate pharmacokinetic profile of the patient, the dosing regimen including a dosage and a dosage interval, modify the dosing regimen in response to receiving another dosing interval for applying the dosage to the patient, and enable the dosing regimen and a time-varying therapeutic plasma protein level based on the dosing regimen to be displayed to a user.

In accordance with a seventeenth aspect of the present disclosure, which may be used in combination with any one or more of the preceding aspects, the machine-accessible device further comprises instructions stored thereon that are configured when executed to cause the machine to determine a first dosing regimen for a two-day dosing interval, determine a second dosing regimen for a three-day dosing interval, and enable the display of the first dosing regimen in conjunction with the second dosing regimen.

In accordance with an eighteenth aspect of the present disclosure, which may be used in combination with any one or more of the preceding aspects, the machine-accessible device further comprises instructions stored thereon that are configured when executed to cause the machine to display a graphical representation of a time-varying amount of the therapeutic plasma protein within the patient, including at least one indication of a dose of the therapeutic plasma protein being provided to the patient.

In accordance with a nineteenth aspect of the present disclosure, which may be used in combination with any one or more of the preceding aspects, the machine-accessible device further comprises instructions stored thereon that are configured when executed to cause the machine to display a graphical feature than enables a user to change at least one of (i) a minimum concentration threshold, (ii) the dosage interval, or (iii) the dosage of the therapeutic plasma protein.

In accordance with a twentieth aspect of the present disclosure, which may be used in combination with any one or more of the preceding aspects, the machine-accessible device further comprises instructions stored thereon that are configured when executed to cause the machine to modify the dosing regimen in response to receiving a change of any one of the items (i), (ii), or (iii).

In accordance with a twenty-first aspect of the present disclosure, which may be used in combination with any one or more of the preceding aspects, the machine-accessible device further comprises instructions stored thereon that are configured when executed to cause the machine to display a graphical representation of a change in the amount of the therapeutic plasma protein within the patient over time based on the change of any one of the items (i), (ii), or (iii).

In accordance with a twenty-second aspect of the present disclosure, which may be used in combination with any one or more of the preceding aspects, the machine-accessible device further comprises instructions stored thereon that are configured when executed to cause the machine to receive a minimum concentration threshold and to display an amount of time the therapeutic plasma protein level is below the minimum concentration threshold.

In accordance with a twenty-third aspect of the present disclosure, which may be used in combination with any one or more of the preceding aspects, the machine-accessible device further comprises instructions stored thereon that are configured when executed to cause the machine to receive patient measurement blood laboratory data including a concentration of the therapeutic plasma protein within the patient after a time from when the therapeutic plasma protein was administered to the patient and modify the approximate pharmacokinetic profile based on the patient measurement blood laboratory data.

In accordance with a twenty-fourth aspect of the present disclosure, any of the structure and functionality illustrated and described in connection with FIGS. 1 to 31 may be used in combination with any of the structure and functionality illustrated and described in connection with any of the other of FIGS. 1 to 31 and with any one or more of the preceding aspects.

BRIEF DESCRIPTION OF THE FIGURES

FIGS. 3 to 13 show diagram that include example user interfaces provided by the drug dosing tool of FIG. 1 to determine a dosing recommendation and estimated pharmacokinetic profile for a specific patient, according to an example embodiment of the present disclosure.

FIGS. 23 to 30 show diagrams of tables and graphs that correlate a concentration of administered therapeutic plasma protein with bleed risk for different patients, according to an example embodiment of the present disclosure.

DETAILED DESCRIPTION

Figure 1:
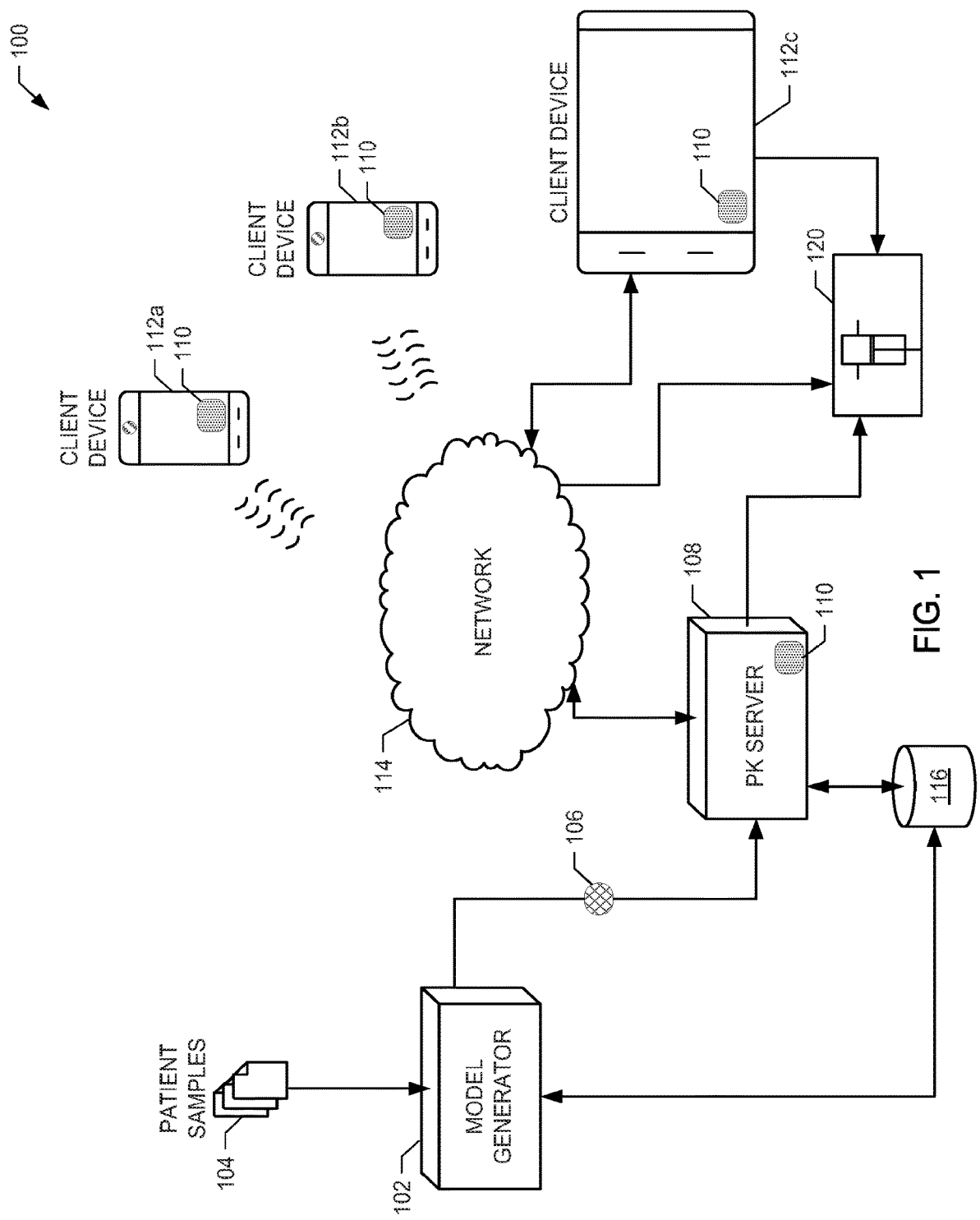
FIG. 1 shows a diagram of an example pharmacokinetic drug dosing environment, according to an example embodiment of the present disclosure.

The present disclosure relates in general to a method, system, and apparatus to provide a drug dosing regimen, and in particular, to provide a pharmacokinetic drug dosing regimen based upon a model of pharmacokinetic profiles of sampled patients. The pharmacokinetic drug dosing regimen described herein provides a cost-effective use of therapeutic plasma protein, which may be tailored to an individual patient. As such, the example pharmacokinetic drug dosing regimen described herein provides healthcare providers with a tool that enables relatively quick and accurate patient dosing recommendations without having to determine a patient specific pharmacokinetic profile based (solely) upon blood testing. The disclosure also contemplates, clotting factor FVIII products that are modified to extend residence mean times in a patient beyond that of native FVIII through, for example, the use of water soluble proteins or FC fusion technology, and dosing schemes/intervals longer than three days.

Presently, healthcare providers formulate a treatment regimen for a patient with low levels of naturally occurring clotting factor VIII by determining a patient specific pharmacokinetic profile to identify how the patient metabolizes a therapeutic plasma protein over time. To determine a patient's pharmacokinetic profile, a healthcare provider performs an initial baseline blood draw before a patient is administered a therapeutic plasma protein. This baseline blood draw is used to determine the amount of naturally occurring clotting factor VIII in the body. The healthcare provider then administers the therapeutic plasma protein and performs three or more blood draws over a 48-hour post-treatment period. Over this time, the patient metabolizes the therapeutic plasma protein such that the concentration of clotting factor VIII within the patient returns to the patient's own naturally occurring level. The healthcare provider analyzes the patient's drawn blood via laboratory analyzers to determine the amount of clotting factor VIII within the patient at each blood draw. This analyzed blood laboratory data enables the healthcare provider to determine how quickly a patient metabolizes the therapeutic plasma protein.

As a general rule, most healthcare providers set a target (widely accepted) threshold such that the clotting factor VIII within a patient does not fall below 1% (i.e., 1 IU/dL). Patients with less than 1% of clotting factor VIII are considered susceptible to uncontrolled or spontaneous bleeds. While this approach works some of the time, many patients have daily, weekly, or even monthly variances in their metabolism and/or tendencies to bleed, and may need different clotting factor FVIII levels to remain bleed free. These variances are oftentimes related to patient body weight, age, joint health, and physical activity level. The dosing regimen determined for the patient usually does not account for these variances, which potentially leaves the patient exposed to bleeds if the clotting factor VIII falls below the generally accepted 1% natural baseline threshold, and/or is lower than needed to prevent bleeds during periods of higher risk/physical activity.

The example method, system, and apparatus disclosed herein account for patient pharmacokinetic variance by creating individual patient profiles based not only on the patient's own intensive pharmacokinetic profiling, but rather a (Bayesian) model that uses pharmacokinetic profiles of a set of sample representative patients and/or and a limited number of patient blood sample data points in conjunction with minimal patient information. The example method, system, and apparatus disclosed herein enable a healthcare provider to refine the model based on a patient's previous treatments and/or an activity level of the patient. Such a configuration enables healthcare providers to create individualized dosing regimens based on knowledge of a population of sampled patients that have similar characteristics as the patient undergoing treatment, thereby reducing the effects of individual pharmacokinetic variance of the patient and reducing (or preventing) the number of bleeds experienced by the patient while on prophylaxis.

The example disclosure includes two primary embodiments. A first primary embodiment includes a drug dosing tool that uses previously collected patient data to establish one or more pharmacokinetic models. The example method, system, and apparatus use this model to determine how a therapeutic plasma protein changes over time in a patient based upon the patient's physical attributes (e.g., age, body weight, gender, activity level, endogenous clotting factor VIII level, etc.) and previous dosing treatments. A healthcare provider may use the model to determine a drug dosage and dosing interval for the patient.

A second primary embodiment includes a drug dosing tool, such as an application ("App") operating on a mobile computer (e.g., a smart phone or a tablet computer). The application is configured to enable a user (e.g., a drug sales representative) to provide healthcare providers with a graphical interface that displays how a particular therapeutic plasma protein (e.g., a clotting factor VIII such as Shire's ADVATE) performs under different conditions. The example pharmacokinetic drug tool of this second embodiment uses a pharmacokinetic model of sampled patients to enable the user to highlight the benefits of using, for example, an every-three-day dosing scheme, an every-four-day dosing scheme, an every-five-day dosing scheme, etc. instead of an every-one-day or an every-two-day dosing scheme for therapeutic plasma protein. The drug tool uses relationships between therapeutic plasma protein concentrations, therapeutic plasma protein dosage levels, therapeutic plasma protein dosage times, and patient parameters to calculate how the therapeutic plasma protein concentration changes over time for a theoretical patient.

As used herein, the term "clotting factor VIII", "FVIII", or "rAHF" refers to any FVIII molecule that has at least a portion of the B domain intact, and which exhibits biological activity that is associated with native FVIII. In one embodiment of the disclosure, the FVIII molecule is full-length FVIII. The FVIII molecule is a protein that is encoded by DNA sequences capable of hybridizing to DNA encoding FVIII:C. Such a protein may contain amino acid deletions at various sites between or within the domains A1-A2-B-A3-C1-C2. The FVIII molecule may also be an analog of native clotting factor FVIII, wherein one or more amino acid residues have been replaced by site-directed mutagenesis.

The term "recombinant Factor VIII" (rFVIII) may include any rFVIII, heterologous or naturally occurring, obtained via recombinant DNA technology, or a biologically active derivative thereof. As used herein, "endogenous FVIII" includes FVIII which originates from a mammal intended to receive treatment. The term also includes FVIII transcribed from a transgene or any other foreign DNA present in the mammal. As used herein, "exogenous FVIII" or therapeutic plasma protein includes clotting factor FVIII that does not originate from a mammal.

The FVIII molecule exists naturally and in therapeutic preparations as a heterogeneous distribution of polypeptides arising from a single gene product. The term "clotting factor VIII" as used herein refers to all such polypeptides, whether derived from blood plasma or produced through the use of recombinant DNA techniques and includes, but is not limited to FVIII mimetics, fc-FVIII conjugates, FVIII chemically modified with water soluble polymers, and other forms or derivatives of FVIII. Commercially available examples of therapeutic preparations containing FVIII include those sold under the trade names of ADVATE, HEMOFIL M, and RECOMBINATE (available from Shire PLC, Dublin, Ireland). Other preparations comprise primarily a single sub-population of FVIII molecules, which lack the B domain portion of the molecule.

The FVIII molecules useful for the present disclosure include a full-length protein, precursors of the protein, biologically active or functional subunits or fragments of the protein, and/or functional derivatives thereof, as well as variants thereof as described herein below. Reference to clotting factor FVIII is meant to include all potential forms of such proteins and wherein each of the forms of FVIII has at least a portion or all of the native B domain sequence intact.

"Dosing interval," as used herein, means an amount of time that elapses between multiple doses being administered to a patient. The dosing interval for administering a therapeutic plasma protein including clotting factor VIII may be at least about every one, two, three, four, five, six, seven, eight, nine, ten, eleven, twelve, thirteen, or fourteen days or longer. The dosing interval may change based on changing conditions/characteristics of a patient, changes to a minimally acceptable (e.g., target trough) concentration of the therapeutic plasma protein within a patient, and/or changes to a dosage.

Pharmacokinetic Drug Dosing Environment

FIG. 1 shows a diagram of an example pharmacokinetic drug dosing environment 100 that may be implemented in either one or both of the embodiments described above. The environment 100 includes a model generator 102 that is configured to generate one or more patient pharmacokinetic models 106 based upon sampled patient data 104. The environment 100 also includes a pharmacokinetic ("PK") server 108 that is configured to provide patients, healthcare providers, and/or sales representatives with a graphical pharmacokinetic drug dosing tool 110 based upon the one or more pharmacokinetic models 106. In the illustrated embodiment, the PK server 108 transmits the tool 110 to client devices 112 via a network 114 (e.g., an Internet). In other embodiments, the PK server 108 hosts the tool 110, which is accessible by the client devices 112. In these other embodiments, the PK server 108 may include a single server, or alternatively, may be distributed within a cloud computing framework.

The example PK server 108 and/or the model generator 102 may be communicatively coupled to a database 116 configured to store the patient pharmacokinetic models 106. The database 116 may include any type of computer-readable medium, including RAM, ROM, flash memory, magnetic or optical disks, optical memory, or other storage medium. The example database 116 may also store information generated in response to users using the tool 110 including, for example, patient information, dosing regimens, etc. In some instances, the database 116 may be managed by a separate third-party storage provider.

In some instances, the PK server 108 and/or the model generator 102 may be provided by the same server and/or processor and/or operated by the same entity. In these instances, the functionality of the model generator 102 may operate in conjunction with the functionality of the PK server 108. For instance, the model generator 102 may periodically update pharmacokinetic models with therapeutic plasma protein dosing information and/or patient information received in the PK server 108 via the tool 110.

The example client devices 112a, 112b, and/or 112c may include any device capable of displaying or otherwise operating the tool 110. Examples of the client devices 112 include a smartphone, a table computer, a laptop computer, a desktop computer, a workstation, a server, a processor, smart eyewear, a smart watch, etc. In some instances the tool 110 may be installed on the client device 112. In other instances, the tool 110 provides an interface (e.g., a web browser) to functionality configured to reside at the PK server 108. In these instances, the PK server 108 may include one or more application programmable interfaces ("APIs") configured to enable the tool 110 to access the desired data and/or functionality.

Model Generator

In the embodiments described herein, a pharmacokinetic model is used to estimate or approximate pharmacokinetic profiles of patients because precise patient-specific pharmacokinetic profiles are relatively complex or difficult to determine without extensive blood draws to determine clotting factor VIII in circulation. For instance, current methods to determine a patient-specific pharmacokinetic profile for hemophilia A include performing multiple blood tests. These blood tests include performing an initial blood draw to determine a clotting factor VIII baseline in a patient. Then, after therapeutic plasma protein is administered, ten to twelve or more blood draws may be performed over a 48 to 72 hour post-infusion period. As can be appreciated, such a procedure is especially taxing on a patient, healthcare provider, and lab because of the numerous separate blood draws. Accordingly, the example model generator 102 is configured to generate relatively accurate pharmacokinetic models based upon a sample of patients with varying ages, body weights, genders, and activity levels. These models are then used to determine or approximate a pharmacokinetic profile of a patient without having to subject a patient to all of the blood draws and subsequent analysis.

In an embodiment, the pharmacokinetic models 106 are determined using patient samples 104 selected from one or more sets of patient data. The patient samples 104 may be, for example, selected among patients who have already been subscribed a therapeutic dosing regimen using the above described blood draw procedure. The patient samples 104 may also include patients specifically selected to go through the blood draw procedure for the purpose of creating the models. The patient samples 104 may include patients from one hospital or medical system and/or patients associated from multiple hospitals, medical systems, geographic regions, etc.

The patient samples 104 include data for patients of varying ages, body weights (or body mass index ("BMI"), medical conditions, clinical laboratory data, genders, and/or activity levels. In the example described herein, sample patient ages vary between 2 and 100 years of age. In some embodiments, the data for the patients may be separated into children and adult age brackets such that a separate model is generated for each bracket. The patient data may additionally or alternatively be partitioned based on body weight, gender, and/or activity level.

As mentioned, the example patient samples 104 include a determination of clotting factor VIII before therapeutic plasma protein is infused into the patients. Then, post infusion blood samples are collected from each patient after certain durations of time. It should be appreciated that in other examples, the blood samples may be collected at different times and/or the number of blood samples collected may be fewer or greater. For instance, fewer blood samples may be collected from children.

Figure 2:
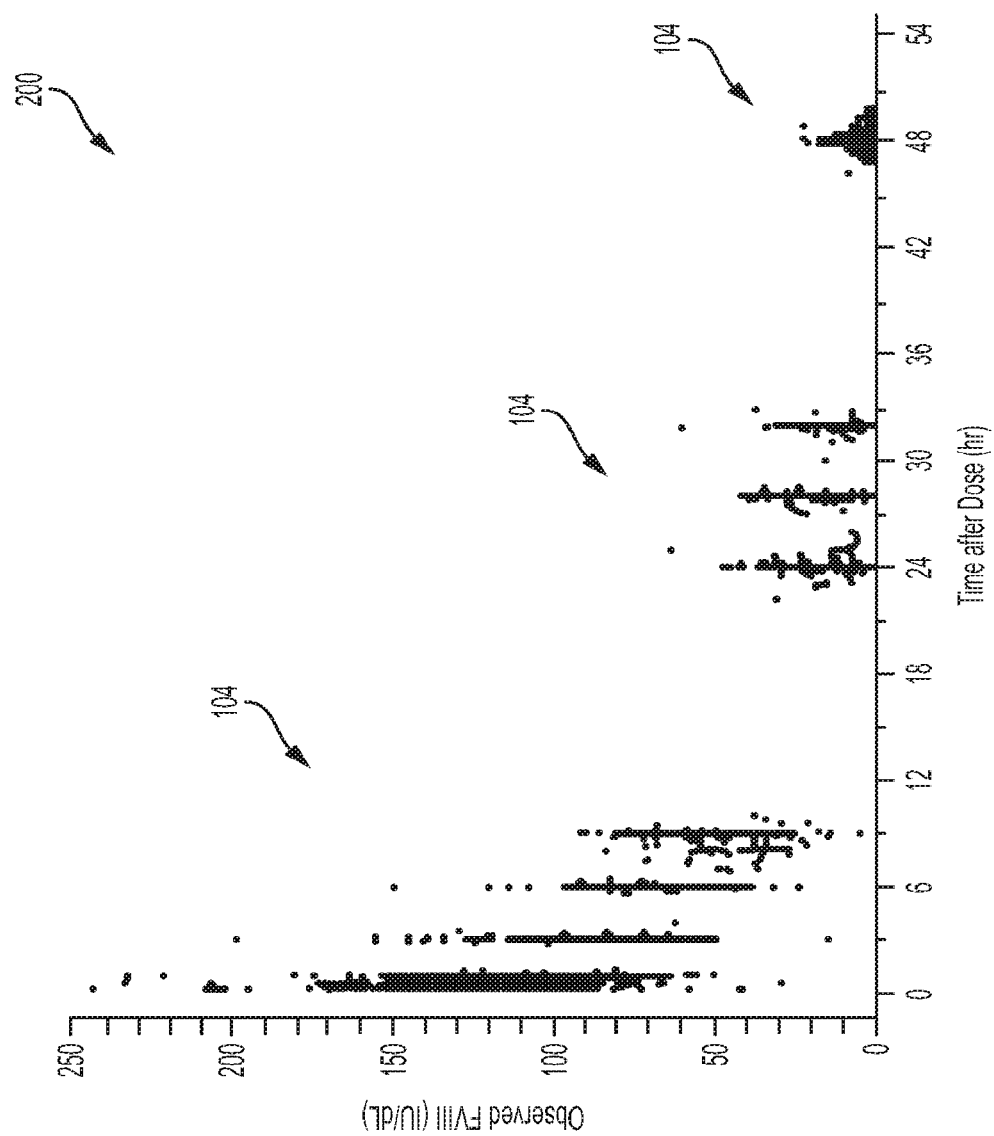
FIG. 2 shows a diagram of patient sample data for a number of patients with hemophilia A, according to an example embodiment of the present disclosure.

FIG. 2 shows a diagram of graph 200 including patient sample data 104 for one-hundred, fifty-two patients with hemophilia A. The sample data 104 is shown as a level of clotting factor VIII in international units ("IU") per deciliter ("dl"). The samples were collected at pre-infusion (shown at time 0) and post-infusion at intervals of 15 minutes, 30 minutes, 1 hour, 3 hours, 6 hours, 9 hours, 24 hours, 28 hours, 32 hours, and 48 hours. It should be appreciated that the amount of the clotting factor VIII provided by the therapeutic plasma protein in the patient decreases over time as the patients metabolize the infused therapeutic plasma protein.

The example model generator 102 creates a pharmacokinetic patient model by performing a Bayesian analysis that uses previous knowledge of clotting factor VIII in the sampled patients over time after an infusion of the therapeutic plasma protein. In some instances, the model generator 102 is configured to analyze each patient's sampled dosing history in conjunction with pre-infusion clotting factor VIII levels, so that washout data is not needed to construct the pharmacokinetic models 106. In other embodiments, the model generator 102 may use patient washout data in conjunction with the post-infusion clotting factor VIII levels to create one or more pharmacokinetic models 106. Patient washout data corresponds to a baseline where the patient does not include the therapeutic plasma protein in their system.

The example model generator 102 creates the one or more pharmacokinetic models 106 using, for example, the patient sample data shown in the graph 200. The model generator 102 may combine the individual patient samples 104 into one or more population profiles (e.g., age sets, body weight sets, activity level sets, endogenous clotting factor VIII level, etc.), which is then used as a basis for the respective pharmacokinetic model 106. For instance, the model generator 102 may group the patient samples 104 for different ages, body weights, and/or activity levels into different sets. The model generator 102 then performs covariate and statistical modeling on the grouped patient samples 104 of each set to create a population pharmacokinetic model 106 for that set, as described in a white paper titled "Population pharmacokinetics of recombinant factor VIII—the relationships of pharmacokinetics to age and body weight", by Björkman et al., the entirety of which is incorporated herein by reference. It should be appreciated however, that the model generator 102 may model the sampled data 104 using other Bayesian analysis techniques (e.g., a naïve Bayes classifier).

In the illustrated example, the covariate model used by the model generator 102 determines relationships between pharmacokinetic parameters (e.g., how quickly therapeutic plasma protein is metabolized, endogenous clotting factor VIII level, etc.) and patient characteristics (e.g., age, body weight, clinical laboratory data, gender, activity level, etc.). The model generator 102 uses a statistical model to determine variance in pharmacokinetic parameters among the sampled patients in addition to residual variance as a result of biological variability between patients, measurement errors, and errors within the fit of the sampled data 104 to the pharmacokinetic model.

The example model generator 102 is configured to perform the covariate and statistical modeling using non-linear mixed effects modeling with a first-order integral approximation method, as provided in SAS® software (NLMIXED procedure). In the illustrated example, the model generator 102 uses a two-compartment model. In other examples, the model generator 102 may use a single compartment model or three or more compartment models. In the illustrated two-compartment example, the first compartment includes pharmacokinetic parameters of clearance ("CL") and volume of distribution (V1).

CL refers to the amount of time for a patient to metabolize the therapeutic plasma protein in milliliters ("mL") per hour per kilogram ("kg"). In other words, clearance is a measure of a rate at which a therapeutic plasma protein is removed or eliminated from a patient. The model generator 102 uses example equation (1) to determine CL, where BW denotes body weight, i denotes the specific sampled patient, and η denotes statistical inter-patient variability.

$$CL_i(\text{mL/h}) = 193 * \left(\frac{BW_i}{56}\right)^{0.80} * (1 - 0.0045 * (\text{Age}_i - 22)) * \exp(\eta_i^{CL}) \quad (1)$$

V1 refers to a theoretical volume that the therapeutic plasma protein would have to occupy to provide the same concentration as it is currently in a patient's blood. This theoretical volume provides an estimation for a dose to achieve a certain clotting factor VIII level. The model generator 102 uses example equation (2) to determine V1. In the example described herein, V1 is about 0.4 L/kg.

$$V1_i(L) = 2.22 * \left(\frac{BW_i}{56}\right)^{0.95} * \exp(\eta_i^{V1}) \quad (2)$$

The second component of the illustrated model includes an inter-compartmental clearance ("Q") and a second volume of distribution ("V2"), which does not account for inter-patient variability. The model generator 102 uses example equation (3) to determine Q and equation (4) to determine V2. The inter-compartmental clearance Q is used in conjunction with clearance CL to determine a scaling relation of the second volume of distribution V2 to the first volume of distribution V1. In this example, the inter-compartmental clearance Q is not significantly related to body weight, indicating that V1 and V2 are cumulative for determining a volume of distribution at steady state. In other words, the total volume of distribution is determined by adding V1 and V2. In one implementation, the average total volume of distribution of the patient samples was found to be about 0.053 L/kg.

$$Q_i(\text{mL/h}) = 147 \quad (3)$$

$$V2_i(L) = 0.73 * \left(\frac{BW_i}{56}\right)^{0.76} \quad (4)$$

After generating the model 106 provided by example equations (1) to (4) above, the example model generator 102 may verify the model by determining individual values for CL, Q, V1, V2, and V1+V2 for each sampled patient and comparing the results to the model. Such a comparison provides an indication as to the accuracy of the model. In some examples, the model generator 102 may determine a statistical distribution of the sampled patient data to determine whether the model is accurate. In instances in which the model does not appear to be accurate, the model generator 102 may compile additional patient samples 104 and/or perform other modeling techniques.

Responsive to creating one or more pharmacokinetic models 106, the model generator 102 provides the pharmacokinetic model(s) 106 to the PK server 108. The transmission may be over a private network, such as a local area network, or over a public network, such as an Internet. The model generator 102 may also store the models 106 to the database 116, which is also accessible by the PK server 108 via one or more interfaces. In other instances, the model generator 102 may be integrated with the PK server 108.

In addition to providing the pharmacokinetic models 106 based upon equations (1) to (4) above as applied to samples of random patients, the example model generator 102 may refine the models for each patient whose therapeutic plasma protein dosing is calculated using the drug dosing tool. For instance, the PK server 108 may receive patient specific information including, body weight, age, gender, endogenous clotting factor VIII level, and dosing level for previous treatments. The model generator 102 uses the previous treatment information (e.g., dosing amounts, intervals, etc.) to refine or adjust the model such that dosing recommendations and a pharmacokinetic profile are more aligned to the specific patient but still account for potential patient variance. The model generator 102 transmits the patient-specific model to the PK server 108.

Alternatively, the PK server 108 may be configured to create patient-specific models using the pharmacokinetic model 106 provided by the model generator 102 to account for the patient-specific pharmacokinetic variance. In this manner, one or more base models 106 are refined or adjusted by the PK server 108 responsive to receiving previous treatment information for a specific patient. The PK server 108 may be configured to store the patient-specific model to the database 116 for subsequent uses by the same healthcare provider or other healthcare providers.

In yet other embodiments, the example tool 110 may be configured to adjust or refine a pharmacokinetic model based upon patient-specific treatment information. For instance, the tool 110 may include fields for a user to provide previous treatment information. The example tool 110 uses this previous treatment information when determining a pharmacokinetic profile and dosing recommendations for a patient. Additionally or alternatively, the tool 110 may use treatment information from multiple patients to refine and/or adjust the model 106.

Patient-Specific Tool Embodiment

As discussed above, the PK server 108 can be configured to provide different embodiments of the drug dosing tool 110. FIGS. 3 to 13 include diagrams of example user interfaces provided by the drug dosing tool 110 to determine a dosing regimen and estimated/approximate pharmacokinetic profile for a specific patient using one or more pharmacokinetic models 106. It should be appreciated that the user interfaces may be modified in appearance and/or function based upon the configuration of the drug dosing tool 110. For instance, the graphical elements of the user interfaces may be modified based upon a type of client device 112 (e.g., a smart phone display, a tablet display, a personal computer display).

FIG. 3 includes a diagram of a user interface 300 that includes user registration fields to enable a healthcare provider to access the drug dosing tool 110. The interface 300 includes data fields for user information (e.g., name, practice, address, contact information). In addition, the user interface 300 includes a field for a drug enforcement administration ("DEA") number, which is used by the PK server 108 to validate that the user is an authorized healthcare professional. In instances in which a healthcare professional does not have a DEA number, the professional may contact customer support to manually setup an account to use the tool 110.

Figure 4:
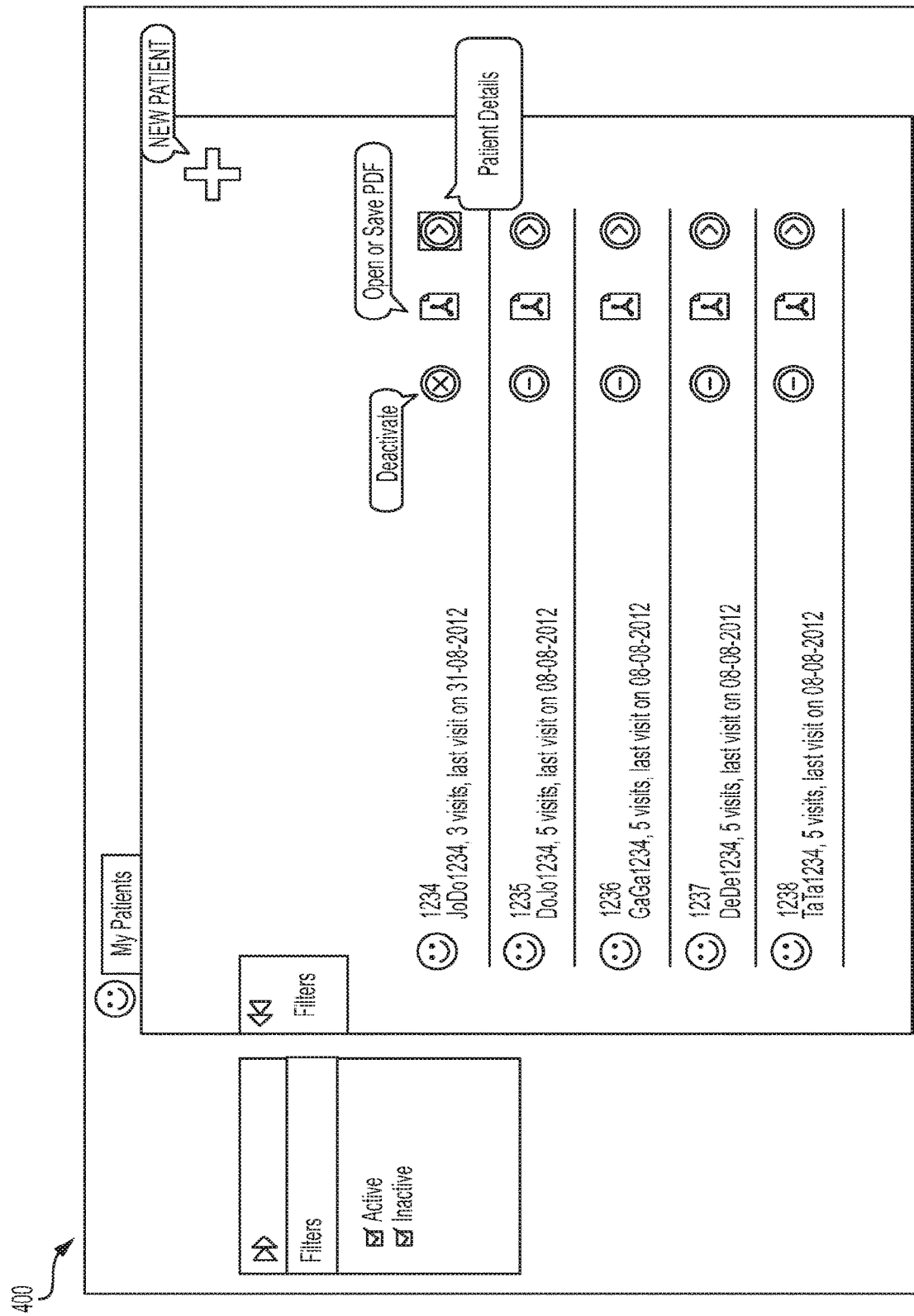

Responsive to receiving the user-provided information in FIG. 3 (including a proper DEA number), the example PK server 108 is configured in the illustrated embodiment to create a user account, which includes a user dashboard. FIG. 4 includes a diagram of user interface 400 for a patient information portion of the dashboard. The user interface 400 provides user management of patients under care of the user. A user uses the user interface 400 to add a new patient, reactivate a current patient, open a report providing details regarding previous treatments (including previous determined pharmacokinetic profile and dosing recommendation), or open a report of patient information. To add a patient, drug dosing tool 110 may provide another user interface that prompts a user for patient information including name, address, insurance information, age, gender, body weight (or BMI), medical conditions, clinical laboratory data, etc.

Figure 5:

For any patient, the drug dosing tool 110 enables a user to determine an estimated/approximate pharmacokinetic profile and dosing recommendation. FIG. 5 includes a diagram of a user interface 500 associated with a new patient visit. In this illustrated example, user interface 500 includes fields for patient information regarding the infusion of therapeutic plasma protein. In instances in which the patient is already registered with the tool 110, at least some of the fields may be pre-populated. Additionally, the 'Dose for PK infusion' field may be populated by the tool 110 responsive to the user progressing through the steps to determine an estimated pharmacokinetic profile and dosing recommendation for the patient.

The example drug dosing tool 110 may also be configured to warn a user if information provided exceeds a predetermined threshold. For example, the tool 110 may be configured to provide a warning message if the pre-infusion level exceeds 20 IU/kg. This warning provides an indication to a user that the entered value is not typical for that field. However, a user may nevertheless continue to use the tool 110 with the information that caused the warning to be generated. Alternatively, the tool 110 may be configured to only accept information within the predetermined range.

After providing a patient name, body weight, birth date, infusion date, and washout or pre-infusion level information, the example drug dosing tool 110 prompts a user to progress to the next step. FIG. 6 includes a diagram of a user interface 600 that is displayed subsequent to a user's provision of information into the user interface 500 of FIG. 5.

The example user interface 600 provides a review of previous patient treatments and/or samples including pre-infusion (or washout) information and dosage (i.e., PK Infusion). A user can select to use the data from one or more previous treatments and/or samples with the tool 110 to refine or adjust the pharmacokinetic model 106 for a patient. A user makes this selection by toggling the 'On/Off' buttons on the right-hand side of the interface 600. For instance, a user may deactivate previous treatments and/or samples that occurred over three years in the past. As a result of this selection, the tool 110 only uses the activated previous treatments and/or samples in refining the pharmacokinetic model 106. This configuration of the tool 110 thereby enables a user to refine a pharmacokinetic model as desired using only specified previous patient treatments and/or samples. In some instances, the user may select to deactivate all previous treatments and/or samples, thereby causing the tool 110 to use the pharmacokinetic model 106 as provided by the model generator 102.

In the illustrated embodiment, three patient samples are shown for a treatment with a therapeutic plasma protein. Each of the samples corresponds to a blood draw of the patient at a time from an infusion treatment of the therapeutic plasma protein. For instance, the first sample was collected 6 hours after the infusion, the second sample was collected 24 hours after the infusion, and the third sample was collected 30 hours after the infusion. The sample information includes a determination of a concentration of clotting factor VIII within the patient's blood at the time the sample was collected. It should be appreciated that the use of the pharmacokinetic model 106 in conjunction with certain selected patient samples may refine a determined patient pharmacokinetic profile to be specific for a patient while also compensating for patient variation common within a sampled population.

After selecting which treatments and/or samples are to be included within pharmacokinetic model 106, the drug dosing tool 110 prompts a user to select a 'Next Step' button, causing the example tool 110 to display user interface 700 of FIG. 7. The example user interface 700 provides a review of which previous treatments and/or samples are to be included in the determination of the estimated pharmacokinetic profile and dosing recommendation for the patient. The selected previous treatments and/or samples may be used to provide a body weight to a dosing regimen based upon previous provided doses. The user interface 700 prompts the user to select the 'Calculate' button to cause the drug dosing tool 110 (or the PK server 108) to apply the patient specific information to the pharmacokinetic model 106 to determine an estimated or approximate pharmacokinetic profile and dosing recommendation for the patient. In some instances, the tool 110 may not make the 'Calculate' button available until a user has provided at least a predetermined number of (e.g., three) previous treatments and/or samples to ensure that the resulting determination is more specific to the patient. It should be appreciated that the tool 110 and/or the PK server 108 selects a pharmacokinetic model of available pharmacokinetic models that best matches the patient information provided within the user interface 500 and/or other user interfaces that prompt a user for patient-specific information. For instance, the pharmacokinetic model may be selected based on a patient's age, body weight, gender, and/or activity level.

FIG. 8 includes a diagram of the user interface 700 of FIG. 7, which now displays the determined pharmacokinetic profile of the patient after calculation by the tool 110 and/or the PK server 108. The 'Theoretical' fields correspond to data that is based solely on the pharmacokinetic model 106 without the previous patient treatments and/or samples. The 'Adjusted' fields correspond to pharmacokinetic profile data specific to the patient based upon the pharmacokinetic model 106 adjusted with the previous treatment and/or sample information. The 'Offset' fields correspond to differences between the respective 'Theoretical' and 'Adjusted' fields. In the illustrated example, the pharmacokinetic profile data includes a clearance of the therapeutic plasma protein, volume of distribution (vdBeta), maximum concentration that the therapeutic plasma protein may achieve after dosing (CMax/Peak), half-life of the therapeutic plasma protein (FVIII half-life), and a time to a minimum (or lower) pre-specified threshold of the concentration of the therapeutic plasma protein within the patient. It should be appreciated that in other embodiments, the user interface 700 can include fewer fields or additional fields for the pharmacokinetic profile including V1 and V2 and/or assay type.

In some instances, the example tool 110 may provide a warning and/or alert if any of the pharmacokinetic profile data is outside of a certain percentage of a sampled patient population used for creating the pharmacokinetic model 106. For instance, the tool 100 may indicate that the adjusted clearance value is outside of 95% of clearance values of sampled patients within the same population set as the patient undergoing treatment. The warning and/or alert may be used as a trigger by a user to verify entered patient information. The warning and/or alert may also be used as an indication that the dosing regimen is abnormal or outside of dosing regimens for sampled patients with similar characteristics as the patient undergoing treatment.

Figure 9:
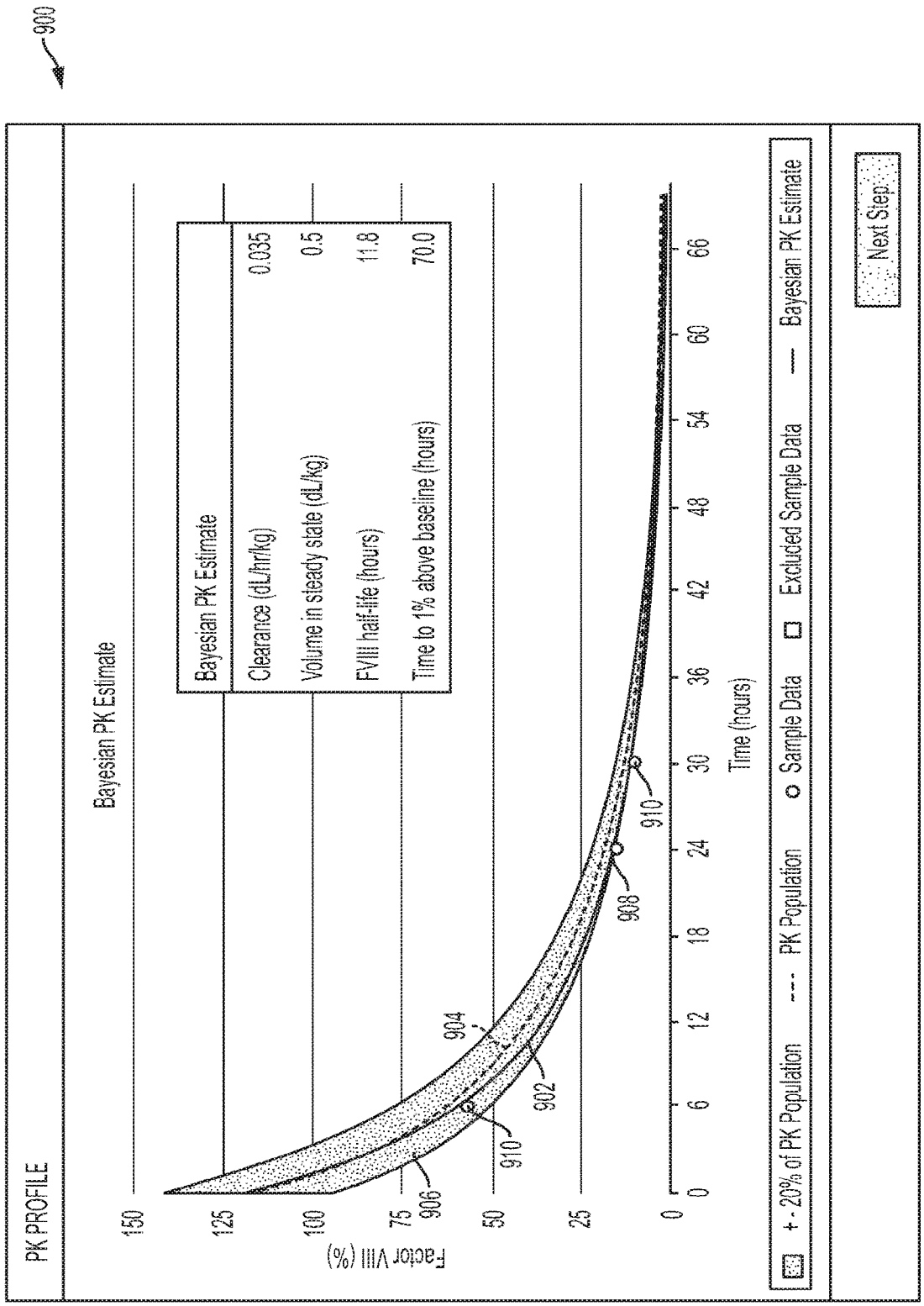
Figure 10:
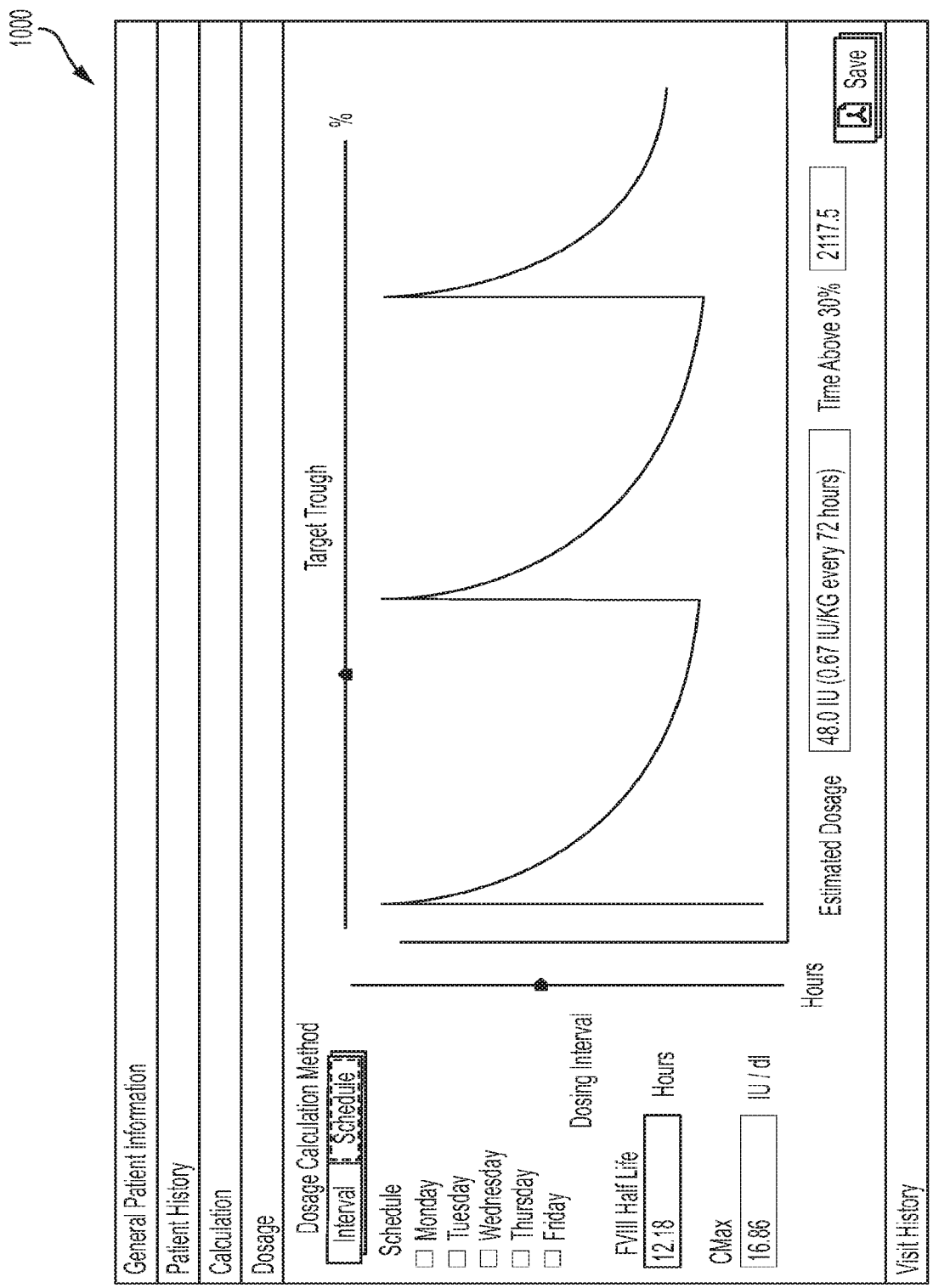

In addition to providing the pharmacokinetic profile data shown in FIG. 8, the example tool 110 also provides a graphical representation of the estimated pharmacokinetic profile and a dosing recommendation. FIGS. 9 and 10 include diagrams of user interfaces 900 and 1000 that display dosing and pharmacokinetic information (e.g., time-varying therapeutic plasma protein level in the patient (e.g., CL)) for a specific patient. The therapeutic plasma protein level is shown as a concentration percentage relative to a normal level of clotting factor VIII within a patient. However, in other embodiments, the therapeutic plasma protein level may be shown as a unit of measure.

FIG. 9 includes a diagram of the user interface 900 that graphically displays an estimated or approximate pharmacokinetic profile of a patient 902. The example pharmacokinetic profile 902 shows how a therapeutic plasma protein is metabolized in a patient over time starting at a time when the therapeutic plasma protein is administered. The pharmacokinetic profile of the patient 902 is denoted by the solid line. The example user interface 900 also includes a comparison of the pharmacokinetic profile of the patient 902 to a pharmacokinetic profile of sample patients 904 used to create the pharmacokinetic model 106, which is denoted by the dashed line. The user interface 900 also includes a shaded band 906 that represents ±20% of the pharmacokinetic profile of sample patients 904.

Moreover, the example user interface 900 includes a graphical representation of patient samples 908 and 910 in instances where the patient received one or more blood tests after an infusion of the therapeutic plasma protein. Patient sample 908 corresponds to a sample not selected to be included within the determination of the pharmacokinetic profile of a patient 902 and patient samples 910 correspond to selected samples for inclusion in the determination of the pharmacokinetic profile of a patient 902. The blood tests are performed to determine an amount of therapeutic plasma protein in the patient after an initial infusion and may be performed to further refine the pharmacokinetic profile of a patient 902. For instance, instead of performing five or more blood draws after an infusion, the example PK server 108 and/or tool 110 may be used to create the pharmacokinetic profile of a patient 902 using the data from fewer blood draws in conjunction with the pharmacokinetic profile of sample patients 904 based on the pharmacokinetic model 106.

The example user interface 1000 of FIG. 10 enables a user to graphically view dosing changes based upon changes to dosing interval and/or a minimum (lower) specified threshold of the concentration of the therapeutic plasma protein (e.g., target trough) based on the pharmacokinetic profile of a patient 902 shown in FIG. 9. For instance, FIG. 10 shows a graph of a dosing regimen that visually indicates how an administered therapeutic plasma protein is metabolized based upon the patient's estimated pharmacokinetic profile 902. The dosing regimen includes a dosing interval of 72 hours such that the concentration of the therapeutic plasma protein does not fall below a target trough of 30%. The example drug dosing tool 110 uses this information to calculate an estimated dosage (e.g., 48.0 IU or 0.76 IU/kg) that is to be administered every 72 hours. The example tool 110 also calculates an amount of time that the therapeutic plasma protein level exceeds (e.g., is below) the target trough. In other instances, the tool 110 may provide an indication of time that the therapeutic plasma protein level is below the target trough, which corresponds to an amount of time that a patient is unprotected by the therapeutic plasma protein and susceptible to bleeds.

The example tool 110 is configured to enable a user to adjust the interval and target trough via the interface 1000 and accordingly change the dosing regimen including the dosage and therapeutic plasma protein level over time. It should be appreciated that changing either the interval or the target trough does not change the estimated pharmacokinetic profile of the patient 902. Instead, the example tool 110 applies the selected interval or target trough to the determined pharmacokinetic profile of the patient 902.

The interface 1000 configuration of example tool 100 enables a healthcare provider to determine how dosing changes based upon changes to the interval or target trough. For instance, a healthcare provider can compare dosing regimens for an every-two-day dosing interval and an every-three-day dosing interval (or additional intervals such as an every-day dosing interval) to determine whether a dosing interval can be extended (or reduced) for a patient, thereby requiring fewer visits to a healthcare facility and/or fewer self-treatments. The target trough enables the healthcare provider to determine how a dosing regimen is affected by a desired minimum therapeutic plasma protein level in the patient. For instance, a healthcare provider may determine that a 10% target trough is acceptable for a (relatively active) patient and accordingly sets the target trough on the user interface 1000 to 10%. Responsive to receiving the selection of the target trough, the example tool 110 determines an estimated dosage such that the concentration of clotting factor VIII does not fall below the 10% threshold while maintaining an every-three-day dosing interval. The healthcare provider accordingly uses the tool 110 to determine whether an every-three-day dosing regimen is appropriate for a 10% target trough such that the dosage or CMax does not exceed a safety threshold.

Figure 11:
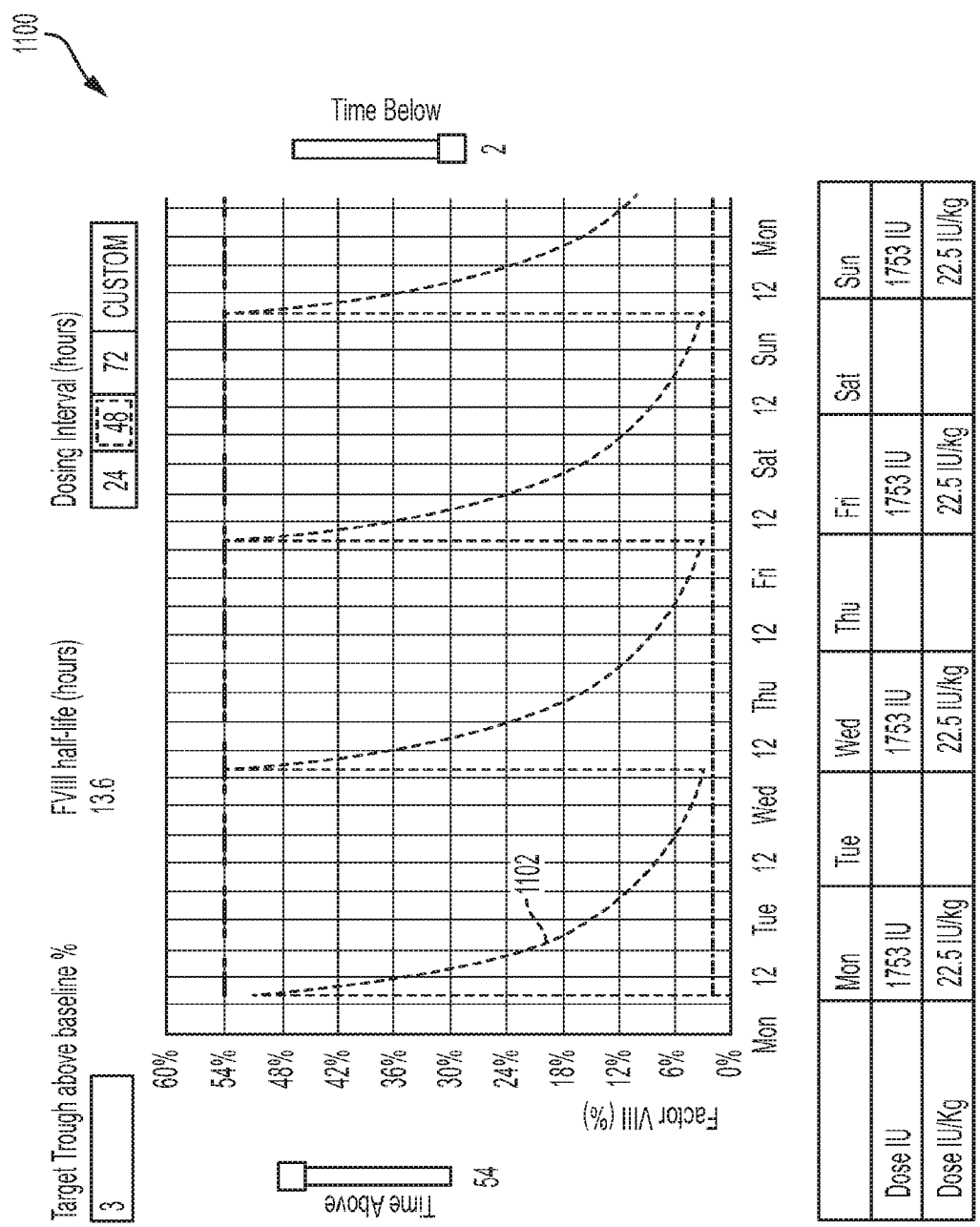

The example drug dosing tool 110 also provides the graphical therapeutic plasma protein level over time and dosage based upon a schedule (e.g., a week, month, year, etc.). For instance, a user can select the 'Schedule' button in the interface 1000, causing the tool 110 to display available days for dosing. A user selects which days a dosage is to be provided to a patient, causing tool 110 to determine a dosage and therapeutic plasma protein level over time such that the therapeutic plasma protein level does not fall below the target trough. For example, FIG. 11 shows a diagram of an example user interface 1100 that enables a user to select particular days (and/or times) for providing a dosage of the therapeutic plasma protein. For example, a user may enter into the tool 110 that a 1753 IU dosage of therapeutic plasma protein is to be provided to a patient on Monday, Wednesday, Friday, and Sunday using a 48 hour dosing interval. A user may select anywhere on concentration line 1102 to view the date/time and specific concentration of clotting factor VIII within the patient.

Figure 12:
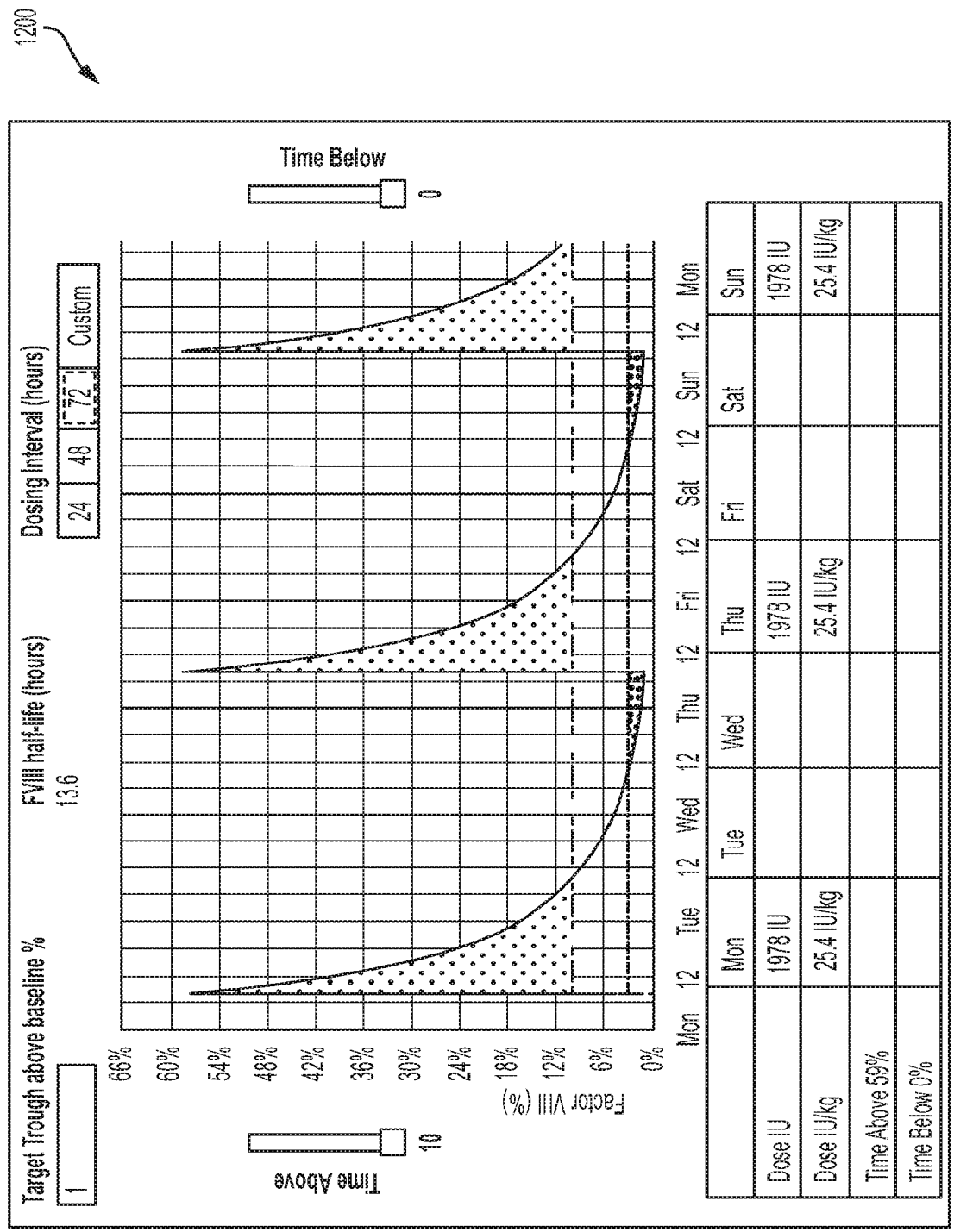

FIG. 12 shows a diagram of a user interface 1200 that enables a user to view amounts of time where the amount of clotting factor VIII is above a specified concentration and below a specified concentration. For instance, a user may select a 'time below' to be 3% and a 'time above' to be 10%. In response to this information, the example tool 110 and/or the PK server 108 determines an amount of time the amount of clotting factor VIII is above 10% and below 3%. The example tool 110 also graphically displays this time within the graph of the user interface 1200. This information shows, for example, an amount of time below 3% where a patient may be left unprotected and is susceptible to bleeds and an amount of time where the patient is fully protected.

Figure 13:
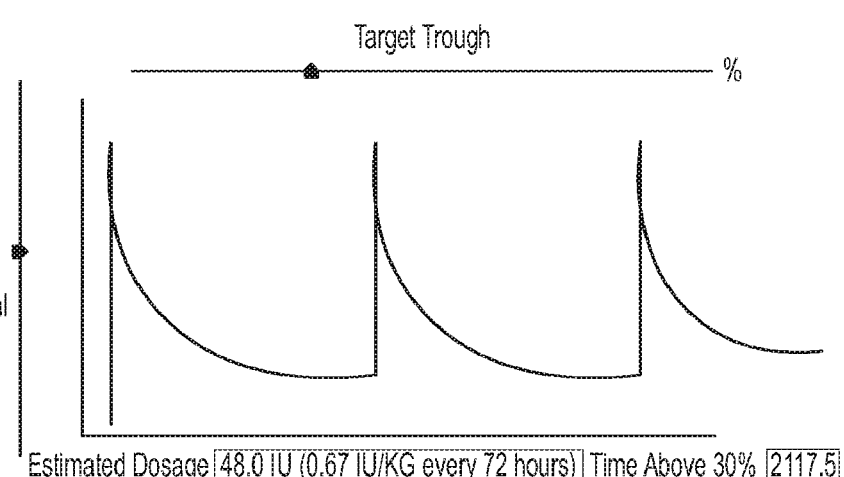

The example drug dosing tool 110 also enables a user to store to the database 116 (and/or a local memory of the client device 112) patient pharmacokinetic profiles in conjunction with dosing and therapeutic plasma protein level data. For instance, a user can select the 'Save' button in interface 1000 of FIG. 10, causing the drug dosing tool 110 to save to a data storage the information described in conjunction with FIGS. 5 to 12. The information may also be saved as a report. FIG. 13 includes a diagram of a report 1300 of the saved information described in conjunction with FIGS. 5 to 12. A healthcare provider may view report 1300 to determine how a dosing regimen of therapeutic plasma protein was calculated for a patient.

In addition to providing patient dosing information, the example tool 110 may be configured in conjunction with the PK server 108 to transmit the dosing information to a hospital information system and/or to an infusion pump 120. For example, returning to FIG. 1, a healthcare provider may use the tool 110 on client device 112c to determine dosing information for a patient. The tool 110 may be configured to transmit the dosing information to the PK server 108. The healthcare provider may also identify an infusion pump that will be providing the dosing. Responsive to receiving the dosing information, the PK server 108 transmits the dosing information to an infusion pump and/or a hospital information system. Alternatively, the PK server 108 may retain the dosing information until requested by an infusion pump. In instances in which a pump is not specified, the hospital information system determines which pump is to provide the infusion to the patient and causes the dosage information to be transmitted to the appropriate pump.

Alternatively, the example tool 110 on the client device 112c may communicate the dosage information directly to the infusion pump 120 (e.g., via near field communication, Bluetooth®, etc.). For instance, the tool 110 may be configured to cause the client device 112c to establish a communication session or to locate a proximately located pump. Upon establishing communication with the pump 120, the tool 110 transmits the dosing information to program the infusion pump.

Additionally or alternatively, the tool 110 may be used directly with a patient. For instance, the example tool 110 may be configured to transmit a schedule to a patient after a healthcare provider has selected a dosing regimen. For example, the tool 110 may transmit a dosing regimen or schedule to the client device 112 of a patient that instructs the patient how much therapeutic plasma protein to infuse and when to infuse. The dosing regimen or schedule indicates (and may include reminders) the specific days (and/or times) of a week, month, year, etc. that the patient is to receive a dosage of the therapeutic plasma protein. Further, tool 110 may be available to a patient to enable the patient to view previous treatments and to compare how a dosing regimen changes based upon a change in dosing interval.

Marketing Tool Embodiment

In the previous embodiment, a healthcare provider uses the example tool 110 to determine a dosing regimen to administer a therapeutic plasma protein to a patient. In a second embodiment, the example tool 110 may instead be configured to provide a generalized dosing regimen (e.g., a dosing regimen for a theoretical patient) to demonstrate to a healthcare provider the capabilities of a therapeutic plasma protein as part of a sales or marketing presentation. For example, a sales representative may demonstrate how the therapeutic plasma protein ADVATE drug performs under every-two-day and every-three-day dosing regimens. The example tool 110 may also compare how a first brand of therapeutic plasma protein performs for a theoretical patient compared to a second brand of therapeutic plasma protein.

FIGS. 14 to 18 display user interfaces provided by the drug dosing tool 110 in this marketing tool embodiment. The user interfaces show theoretical patient data that a sales representative may use to demonstrate to a healthcare provider how therapeutic plasma protein can be prescribed based upon a pharmacokinetic profile of a theoretical patient taking into account the theoretical patient's body weight and half-life time. The half-life time is the time it takes for a drug to reach half its original concentration in a patient.

In particular, the example tool 110 enables a sales representative to demonstrate to a healthcare provider how therapeutic plasma protein performs when the dosing is performed every two days versus every three days for a specified theoretical patient. It should be appreciated that the user interfaces shown in FIGS. 14 to 18 are only example embodiments. In other examples, the layout and/or functionality of the user interfaces may change based upon requirements of sales representatives.

Figure 14:
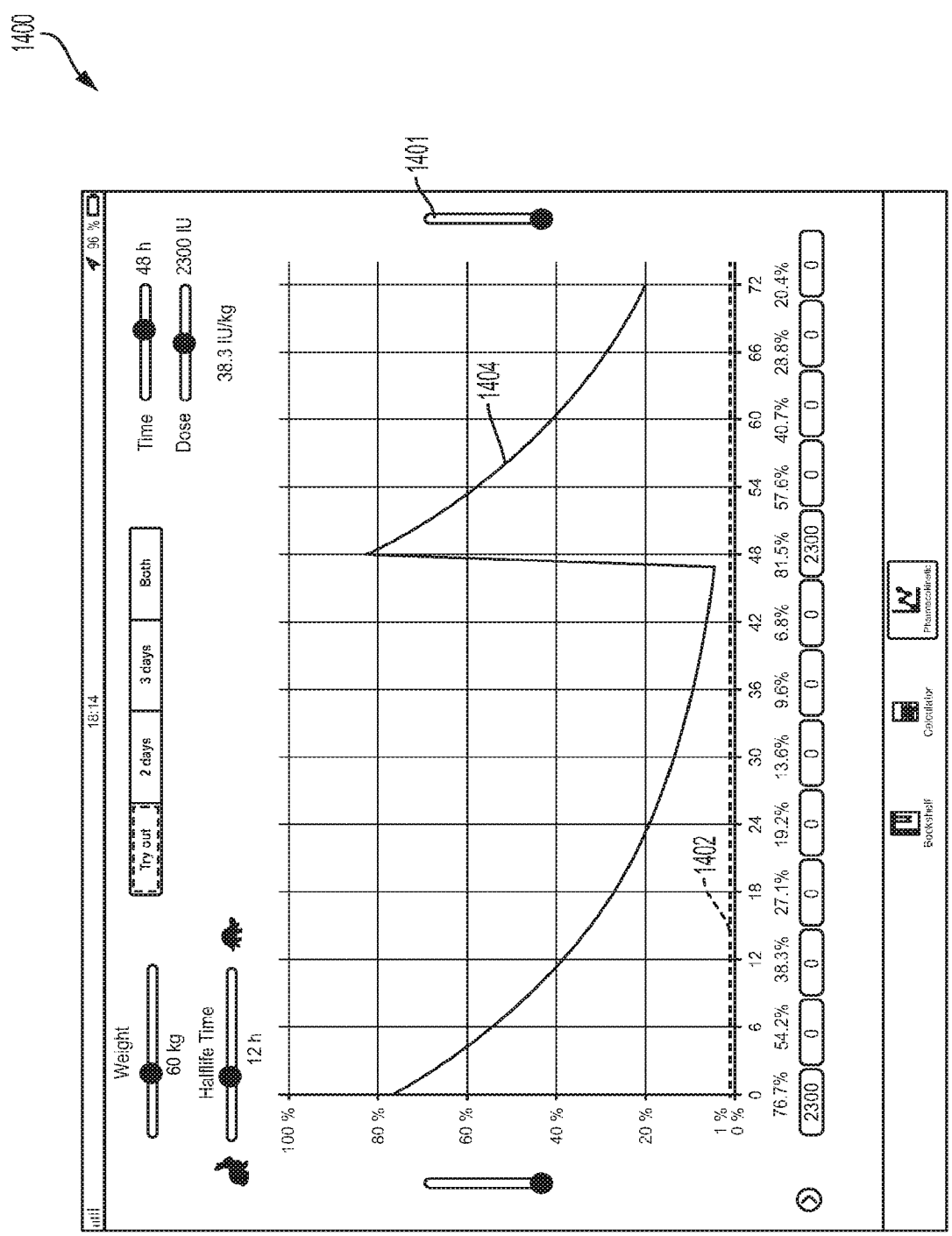
FIGS. 14 to 18 show diagrams that include user interfaces provided by the drug dosing tool of FIG. 1 in a marketing tool embodiment, according to an example embodiment of the present disclosure.

FIG. 14 includes a diagram of user interface 1400 that is provided by the drug dosing tool 110 on the client device 112 of FIG. 1. The interface 1400 is configured to prompt a user to provide a current dosing regimen specified for an actual patient or a theoretical patient. In this illustrated embodiment, a theoretical patient is specified to weigh 60 kg and have a drug half-life of 12 hours. Further, a user specifies a dosing regimen of 2300 IU every 48 hours. Moreover, a user selects a trough threshold (e.g., a minimum or lower threshold) to be 1% using scroll bar 1401. The trough is shown within the user interface 1400 as line 1402.

In response to providing the patient and drug parameters, the drug dosing tool 110 uses a pharmacokinetic model (e.g., the pharmacokinetic model 106 described above) to determine a pharmacokinetic profile of the theoretical patient. The drug doing tool 110 uses this profile to determine a dosing regimen (e.g., dosage and interval). The tool 110 graphically displays the dosing regimen as a concentration of therapeutic plasma protein within the theoretical patient over a time period (shown as line 1404). For example, at time '0', 2300 IU of the drug is shown to be dispensed to the theoretical patient, resulting in a 76.7% concentration of the therapeutic plasma protein in the patient. The concentration of the therapeutic plasma protein decreases over the next 48 hours based upon the determined pharmacokinetic profile of the theoretical patient.

Figure 15:
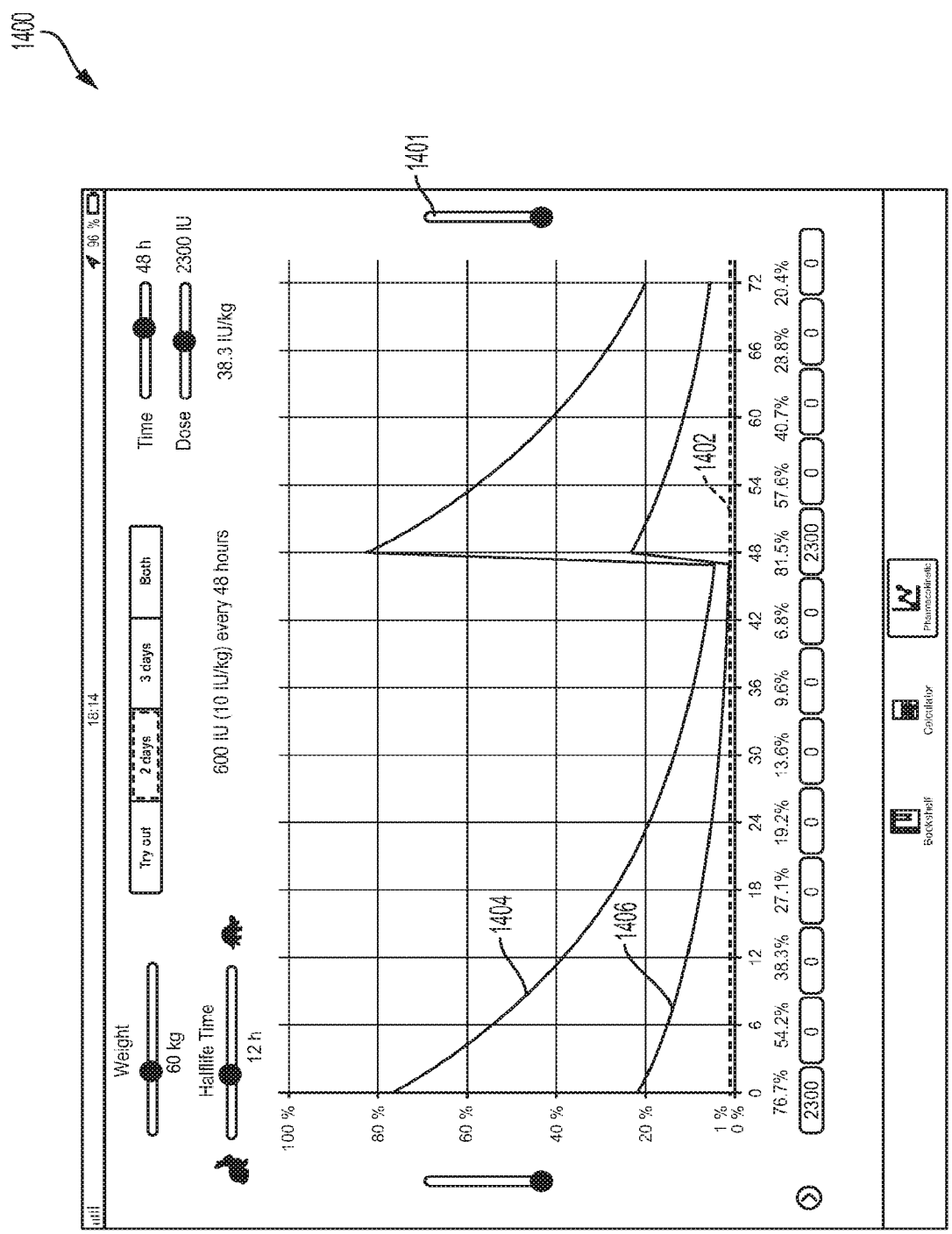

FIG. 15 shows the user interface 1400 of FIG. 14 after a user has selected the '2 days' button. Selection of this button causes the tool 110 to determine an every-two-day dosing regimen based upon the pharmacokinetic profile of the theoretical patient. This regimen includes a dose (e.g., 600 IU) and a graphical display of the therapeutic plasma protein concentration within the theoretical patient over the time period (shown as line 1406). The example tool 110 determines a dose amount for the two day dosing interval such that the concentration of the therapeutic plasma protein does not fall below the specified 1% target trough.

The user interface 1400 of FIG. 15 also provides a comparison of the dosing regimen initially provided by a user and the dosing regimen determined by the tool 110. In the illustrated example, tool 110 graphically indicates that the user only has to prescribe 600 IU instead of 2300 IU every 48 hours. In other words, the tool 110 indicates that the user had overestimated the dosage required such that the concentration of the therapeutic plasma protein does not fall below the 1% target trough.

Figure 16:
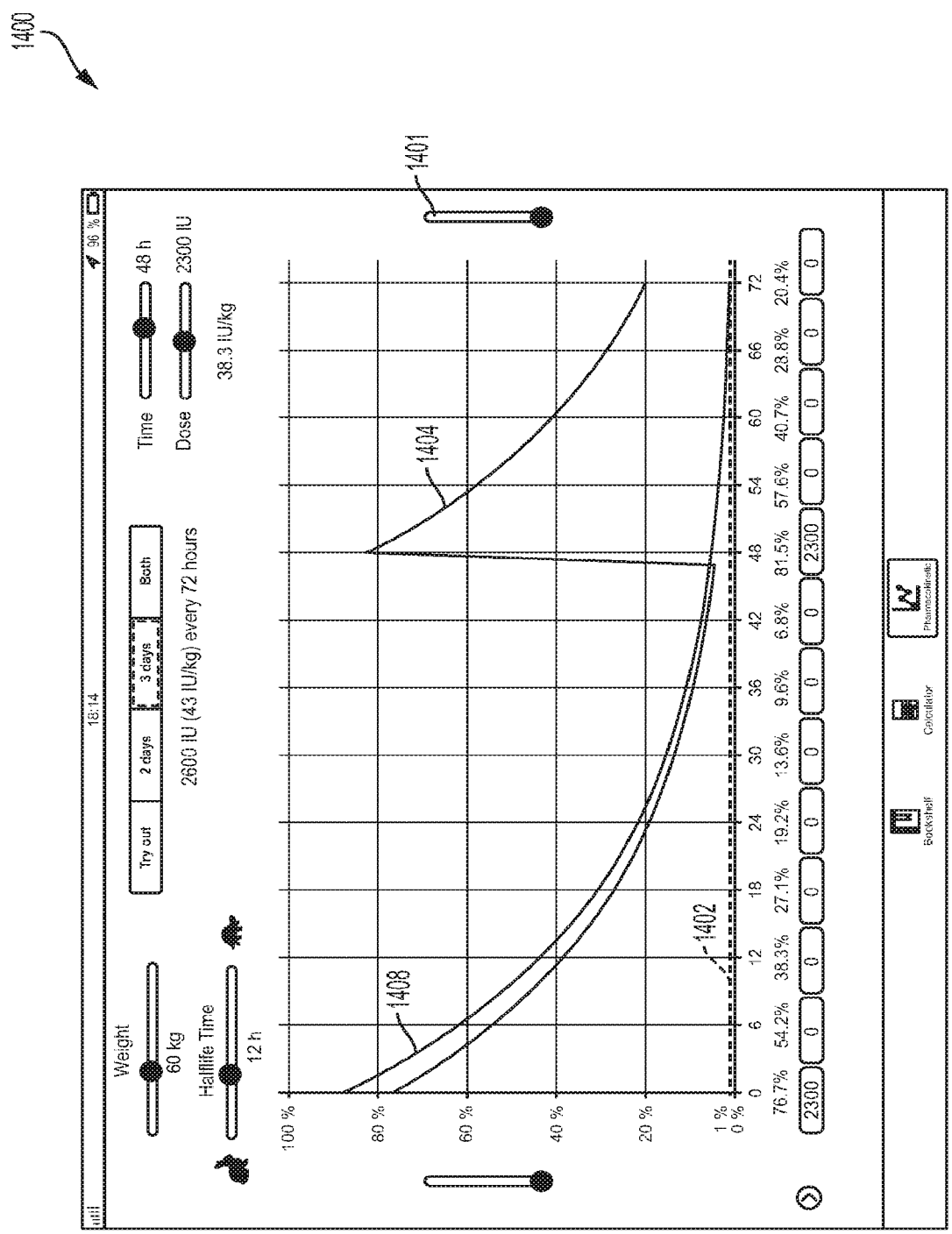

FIG. 16 shows the user interface 1400 of FIG. 14 after a user has selected the '3 days' button. Selection of this button causes the tool 110 to determine an every-three-day dosing regimen based upon the pharmacokinetic profile of the theoretical patient. This regimen includes a dose (e.g., 2600 IU) and a graphically display of the time-varying therapeutic plasma protein concentration within the theoretical patient (shown as line 1408). The tool 110 determines the regimen so that the concentration does not fall below the specified 1% target trough.

The user interface 1400 of FIG. 16 also displays a comparison of the dosing regimen initially provided by a user and the dosing regimen determined using tool 110. In the illustrated example, the tool 110 graphically indicates that a healthcare provider has to prescribe 2600 IU every 72 hours such that the concentration does not fall below 1% during any time between doses. A sales representative can use this graphical comparison to show a healthcare provider that a dosage only has to be increased slightly from a current dosage provided every 48 hours to achieve the same protection from bleeds while increasing the amount of time between doses. It should be appreciated that the extension of the dosing interval places less stress on the patient (e.g., less trips to the healthcare provider) and on the healthcare provider (e.g., fewer doses to administer).

A sales representative uses the graphs displayed in FIGS. 15 and 16 to graphically illustrate to a healthcare provider how a dosing regimen changes for the same theoretical patient using an every-two-day dosing interval and an every-three-day dosing interval. The sales representative can also use the tool to graphically highlight the benefits of using an every-three-day interval by showing that the therapeutic plasma protein can be administered to a patient every three days without violating the 1% threshold. The sales representative may display concurrently the every-three-day interval and the every-two-day interval by selecting the 'Both' button included within the user interface 1400.

Figure 17:
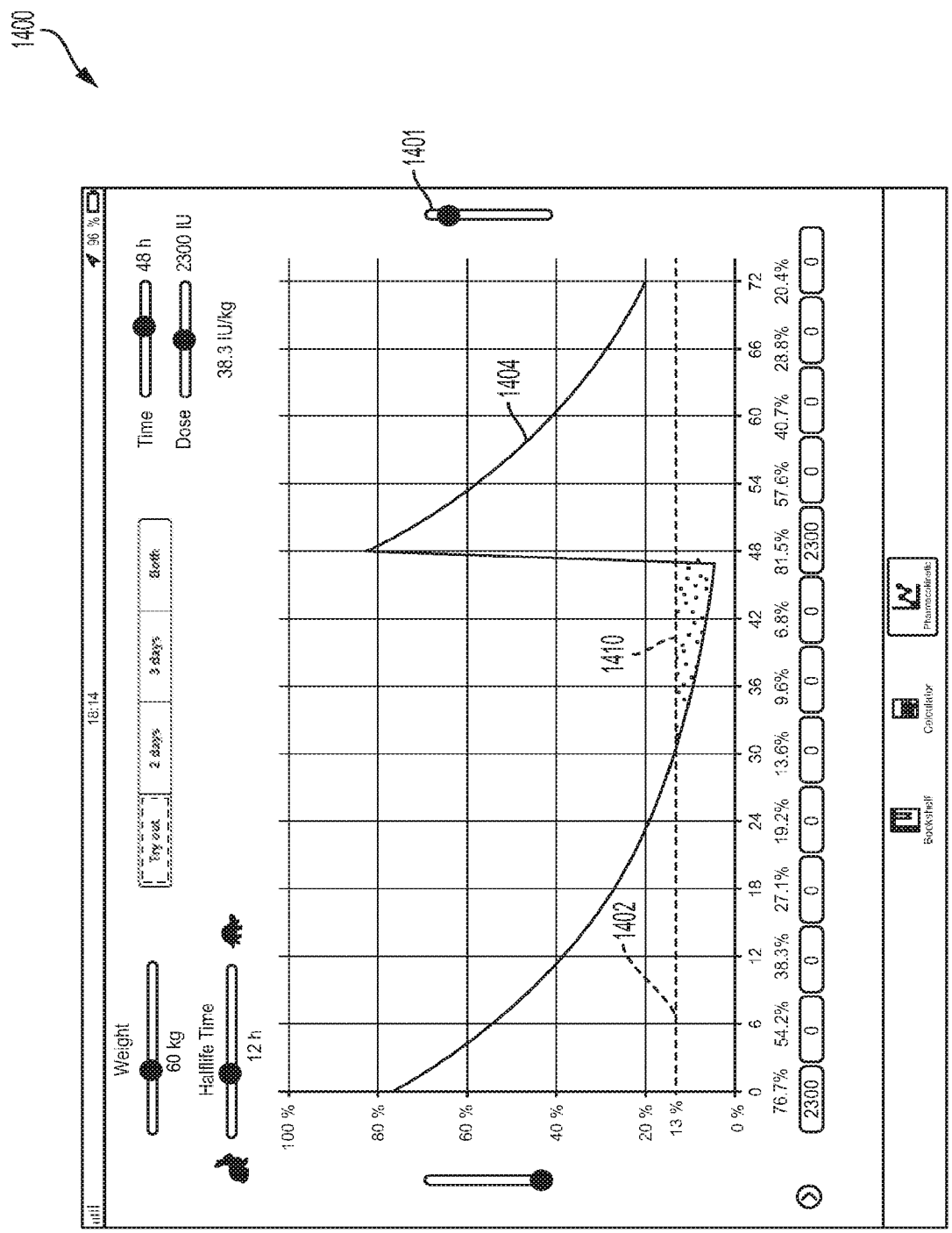

In addition to providing graphical displays of differences between the every-two-day and every-three-day dosing regimens, the example drug dosing tool 110 also graphically shows how long a theoretical patient is left unprotected based upon specified parameters. For example, the user interface 1400 of FIG. 17 shows an indication 1410 displayed by the tool 110 responsive to determining that the time-varying therapeutic plasma protein concentration within the theoretical patient (e.g., the line 1404) falls below the target trough line 1402. In this embodiment, a user raises the scroll bar 1401 such that the target trough is increased to 13%. The example tool 110 determines a duration of time that the therapeutic plasma protein concentration is below 13% and shows this duration at indication 1410. The example tool 110 may also determine a new dosing regimen (e.g., an interval and/or dose) so that the therapeutic plasma protein concentration does not fall below the 13% target trough.

Figure 18:
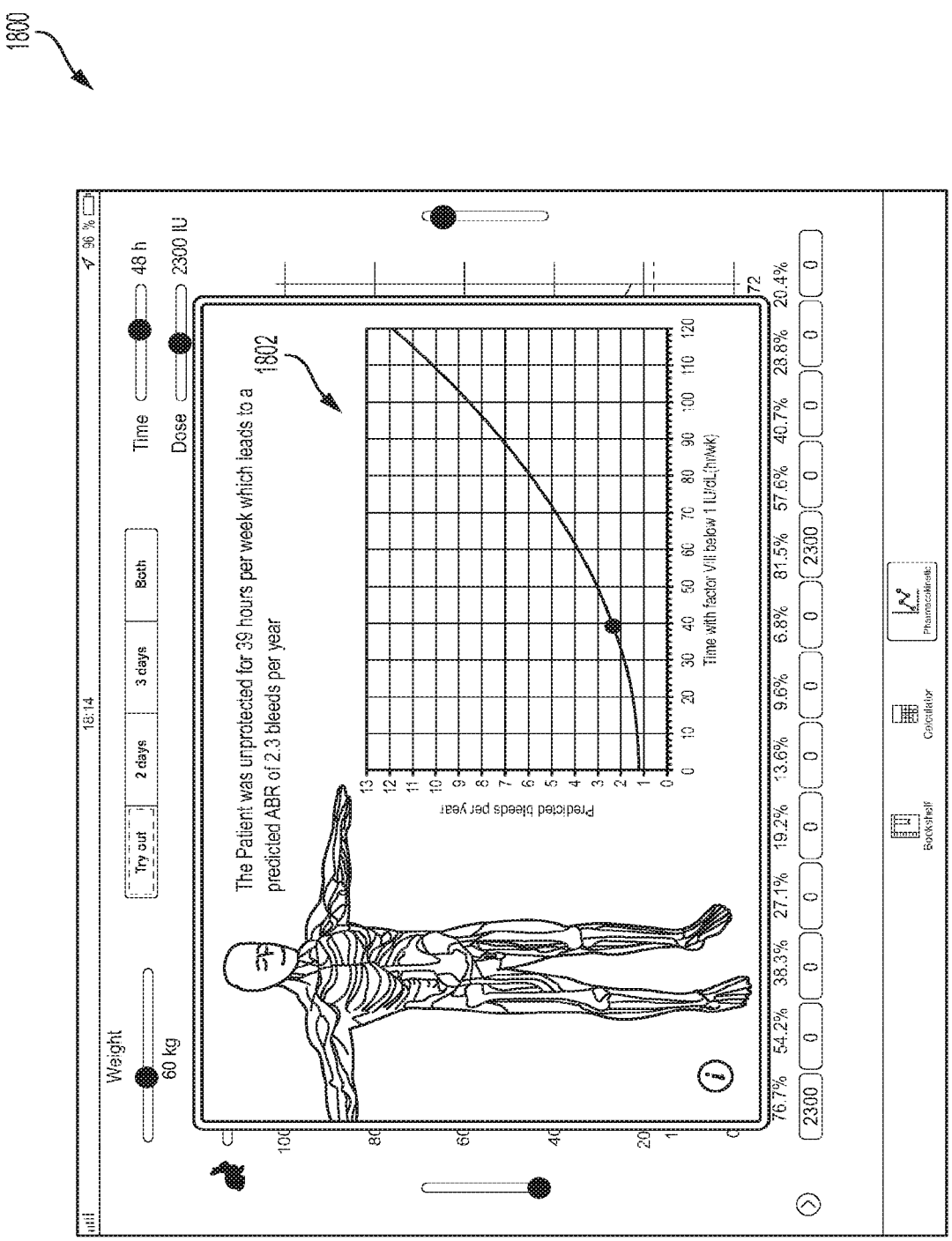

FIG. 18 includes a diagram of user interface 1800 that displays an indication 1802 as to how long a theoretical patient was left unprotected by a therapeutic plasma protein. Indication 1802 is based upon the duration of time that the therapeutic plasma protein concentration resides below the 13% target trough, as determined in conjunction with FIG. 17. The example tool 110 also predicts a number of bleeds a year based upon the duration of time that the therapeutic plasma protein concentration resides below the target trough. In the illustrated example, the indication 1802 includes a graph showing that a theoretical patient would be left unprotected for 39 hours a week, which could result in 2.3 bleeds a year. A sales representative can use the information presented in FIGS. 17 and 18 to show healthcare providers how an every-three-day dosing regimen reduces (or eliminates) times at which a patient is unprotected from the benefits of the therapeutic plasma protein.

Flowchart of Example Drug Dosing Tool Usage Embodiment

Figure 19:
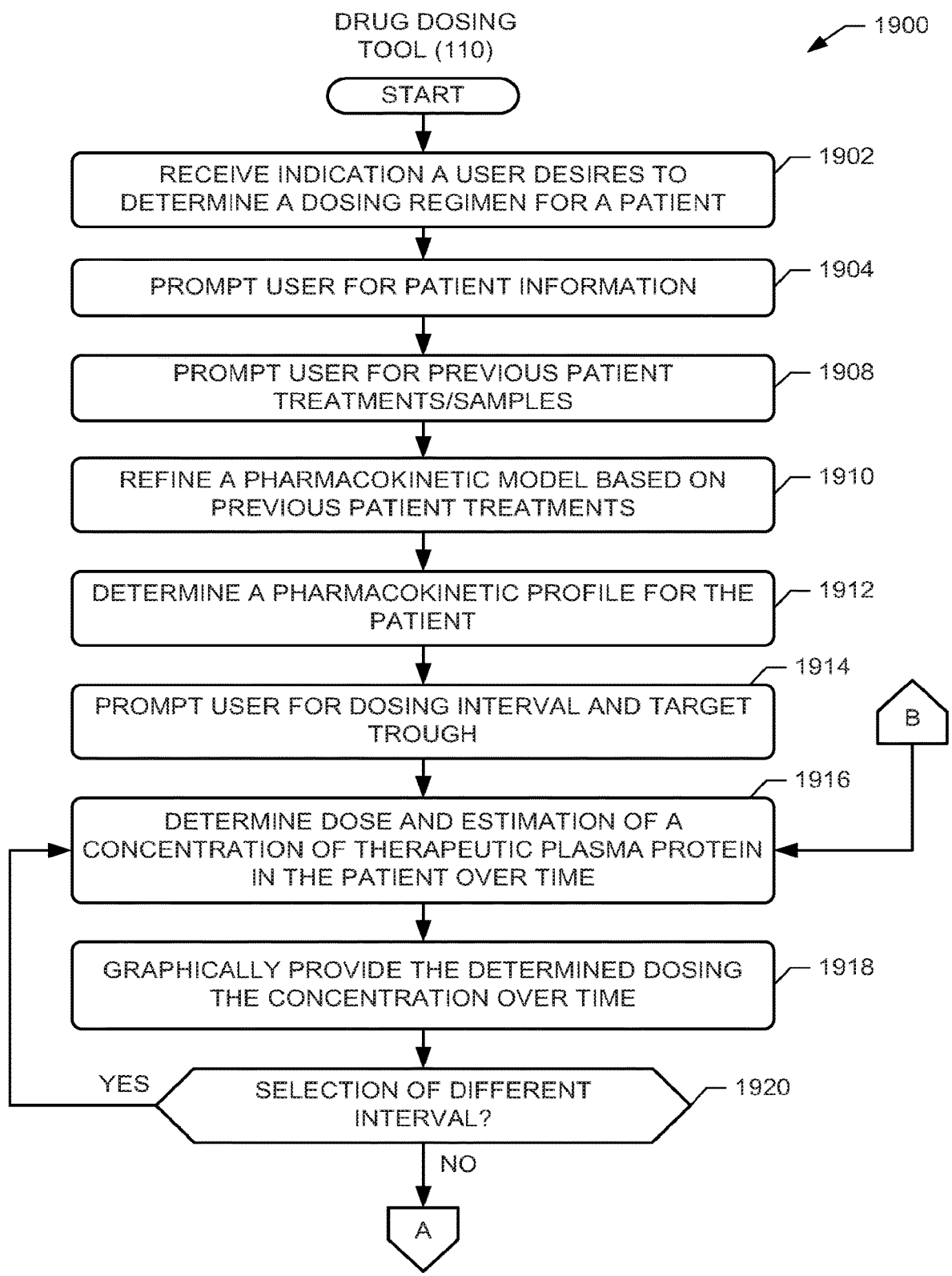
FIGS. 19 and 20 show diagrams that include a flow diagram illustrating an example procedure to determine a dosing regimen, according to an example embodiment of the present disclosure.
Figure 20:
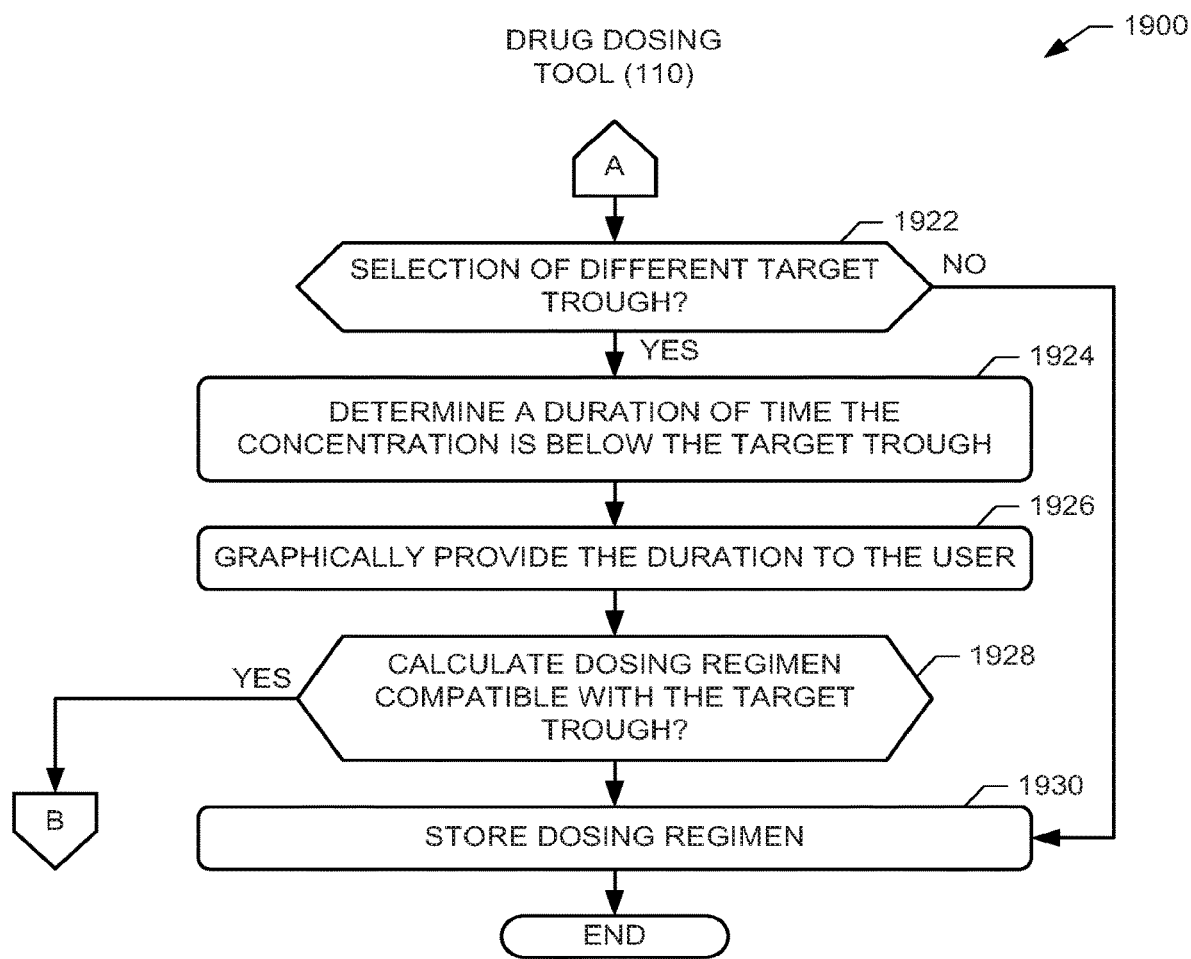

FIGS. 19 and 20 show a flow diagram illustrating example procedure 1900 to determine a dosing regimen for a patient (or theoretical patient), according to an example embodiment of the present disclosure. The example procedure 1900 may be carried out by, for example, the PK server 108 and/or drug dosing tool 110 described in conjunction with FIGS. 1 to 18. Although the procedure 1900 is described with reference to the flow diagram illustrated in FIGS. 19 and 20, it should be appreciated that many other methods of performing the functions associated with the procedure 1900 may be used. For example, the order of many of the blocks may be changed, certain blocks may be combined with other blocks, and many of the blocks described are optional.

Procedure 1900 begins when drug dosing tool 110 receives an indication that a user (e.g., a healthcare provider, sales representative, patient, etc.) desires to determine a dosing regimen (block 1902). The indication can coincide with operating the drug dosing tool 110 on a client device 112 and/or accessing the drug dosing tool on the PK server 108. Responsive to receiving the request for the dosing regimen, the drug dosing tool provides a prompt for patient information (e.g., body weight, gender, age, activity level, etc.) (block 1904). The patient information can correspond to an actual or theoretical patient.

The example drug dosing tool 110 also provides a prompt for previous therapeutic plasma protein treatments for the patient (block 1908). In some embodiments, the drug dosing tool 110 may access the previous treatment information from a stored data structure (e.g., the database 116). The example drug dosing tool 110 accesses and refines a pharmacokinetic model (e.g., the pharmacokinetic model 106) based upon the previous treatments and/or samples (block 1910). It should be appreciated that previous treatment information may not be available or provided to the drug dosing tool 110. In these embodiments, drug dosing tool 110 uses the pharmacokinetic model 106 without modification. It should also be appreciated that in this procedure 1900 the pharmacokinetic model 106 has already been created and provided to the PK server 108 and/or the tool 110. In other examples, the pharmacokinetic model 106 may be created from patient from the samples 104 anytime during and/or before the steps specified in blocks 1902 to 1910).

The example drug dosing tool 110 uses the (refined or modified) pharmacokinetic model and the patient information to determine a (estimated or approximate) pharmacokinetic profile for the patient (block 1912). The drug dosing tool 110 then provides a prompt for a dosing interval and/or a target trough (block 1914). In some instances, the dosing tool 110 may use a default target trough (e.g., 1%) when a trough is not provided or specified by a user. The drug dosing tool 110 next determines a dose of therapeutic plasma protein and an estimation of a concentration of the therapeutic plasma protein in the patient over a specified time period (block 1916). The drug dosing tool 110 graphically provides to the user a dosing regimen including the determined dosing and concentration over time (block 1918).

After providing the dosing regimen, the drug dosing tool 110 in the illustrated embodiment determines if the user has selected a different dosing interval (block 1920). For instance, a user could select to view an every-two-day and an every-three-day dosing interval. If the user provides a different interval, the example drug dosing tool 110 returns to block 1916 and determines a new dosing regimen based upon the selected interval.

However, if the user does not select a different interval, the example drug dosing tool 110 determines whether the user selected a different target trough (block 1922). If the user selects a different trough, the example drug dosing tool 110 determines a duration of time in which the therapeutic plasma protein concentration is less than the trough level (block 1924). The drug dosing tool 110 then provides to the user a graphical indication of this duration (block 1926). The drug dosing tool 110 next determines if the user selects for the dosing tool 110 to determine a dosing regimen based upon the newly provided target trough (block 1928). If the user desires a dosing regimen based upon the new trough, the example procedure 1900 returns to block 1916 and the drug dosing tool 110 determines a new regimen.

However, if a user does not desire to view a new dosing regimen, the example drug dosing tool 110 provides a prompt to store the current dosing regimen (block 1930). Responsive to storing the dosing regimen, the example procedure 1900 ends. Alternatively, (e.g., as selected by the user) the example procedure 1900 returns to block 1902 to determine a dosing regimen for another patient and/or a dosing regimen for the same patient for another visit to the healthcare provider.

Patient Activity Level Example Embodiment

Figure 21:
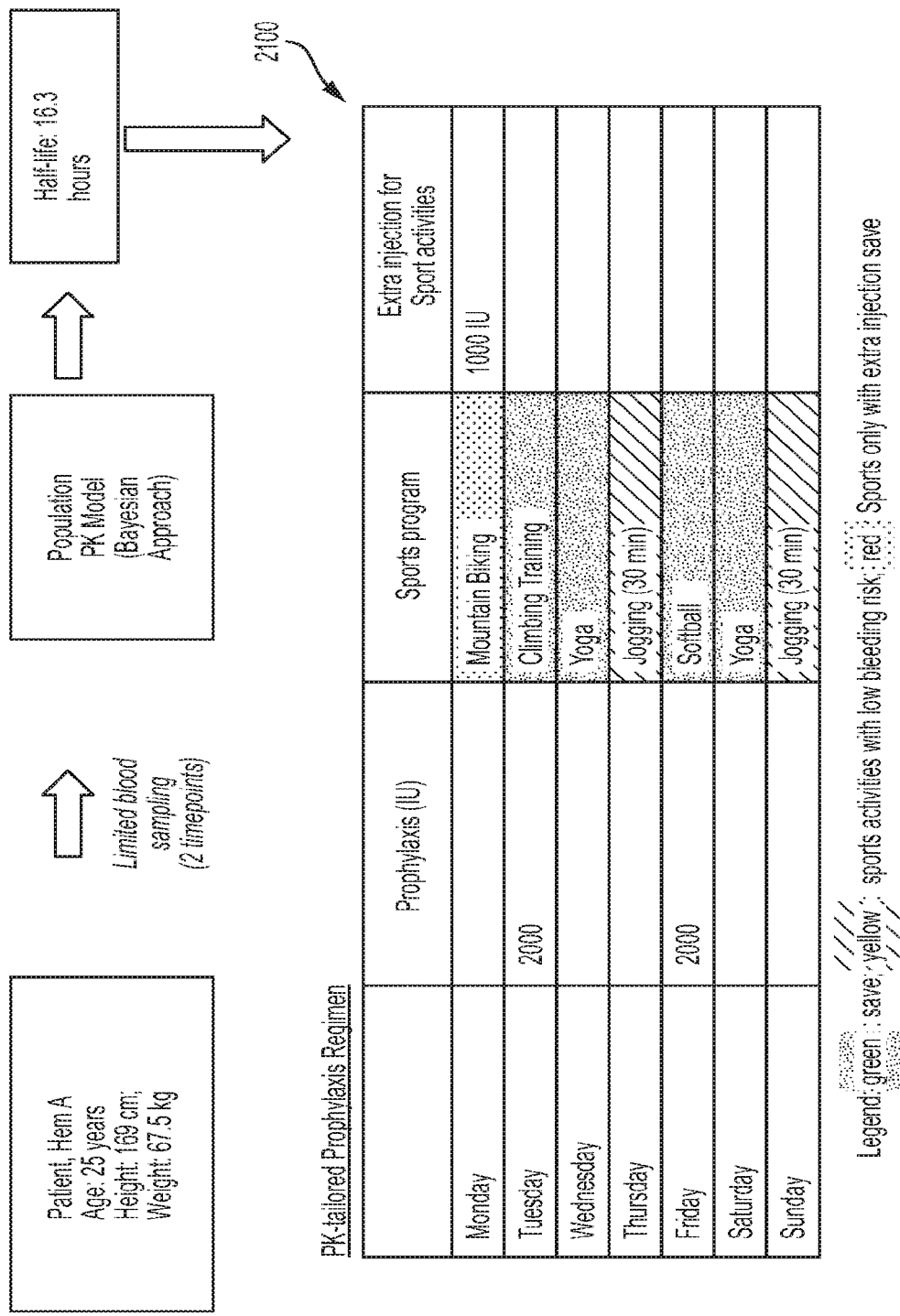
FIGS. 21 and 22 show diagrams that include an example embodiment where a pharmacokinetic profile for a specific patient is adjusted based on activity level.
Figure 22:
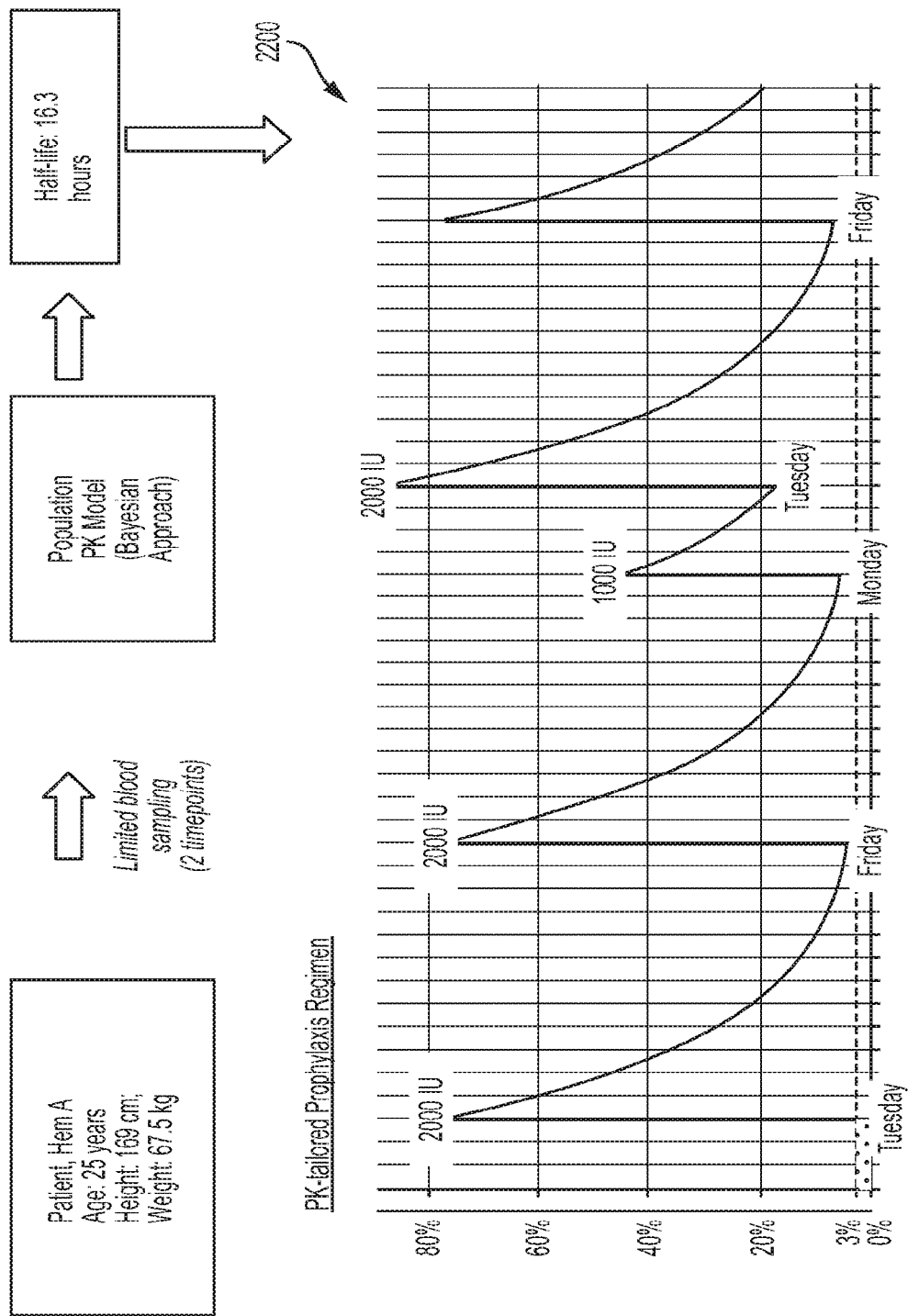

FIGS. 21 and 22 are diagrams that show an example embodiment where a pharmacokinetic profile for a specific patient is adjusted based on activity level. FIG. 21 shows a data structure 2100 that includes a normal dosing regimen in a first column (i.e., Prophylaxis (IU)), an activity level for a patient in a second column, and an adjustment to the dosing regimen in a third column. Each row in the data structure 2100 corresponds to a day of a week.

An estimated or approximate pharmacokinetic profile and the corresponding normal dosing regimen is determined for a specific patient (e.g., Hem A) using the procedures discussed above in conjunction with FIGS. 3 to 13. In this embodiment, the example PK server 108 of FIG. 1 is configured to adjust the normal dosing regimen based on activities of a patient. This adjustment compensates for increases in risk for bleeding as a result of an increased activity level, which increases the need to maintain the therapeutic plasma protein level in the patient above a higher threshold. As discussed above, the amount or concentration of therapeutic plasma protein within a patient is dependent on the patient's metabolism.

To compensate for these temporary increases in risk, the example PK server 108 may prompt a patient or healthcare provider for a weekly schedule of activities. In other instances, the PK server 108 may receive a schedule via an electronic calendar or activity log managed by a patient. In this embodiment, the activities are classified by intensity such that with lower intensity activities separated from activities with relatively greater intensities. The intensity may also be based on a duration of the activity. The PK server 108 may include a data structure that relates different activities with a corresponding intensity level (with adjustments made for duration).

The example PK server 108 uses the activities and associated intensities to adjust the normal pharmacokinetic profile of the patient to determine a modified pharmacokinetic profile based on temporary periods of increased bleeding risk. The PK server 108 then compares the modified pharmacokinetic profile to determine if there is a time period in which the calculated therapeutic plasma protein concentration falls below a target trough. If a time period is determined in which the concentration falls below the target trough, the PK server 108 determines when and how much of an extra dosage of therapeutic plasma protein is to be provided to the patient. In other instances, the PK server 108 and/or the tool 110 may use a pharmacokinetic model 106 that includes sample patients with similar active lifestyles as the patient under care.

In the example of FIGS. 21 and 22, the PK server 108 determines that an activity planned for Monday (e.g., Mountain Biking) is relatively intense, which increases the need to keep the concentration of the therapeutic plasma protein above a target trough level (e.g., 3%). The PK server 108 accordingly determines that an extra dosage of 1000 IU is to be administered to the patient on Monday so that the concentration of the therapeutic plasma protein does not fall below 3%.

FIG. 22 shows a graph 2200 of the modified pharmacokinetic profile based on temporary changes in activity related bleed risk. The graph 2200 shows that before the first Tuesday (before the extra dosage is applied), the concentration of therapeutic plasma protein in the patient falls below 3%. The graph 2200 also shows that before the second Tuesday, 1000 IU is provided to the patient on Monday. This extra dosage causes the concentration of therapeutic plasma protein to remain above the 3% target trough. In this manner, the example PK server 108 reduces the chances of a bleed for relatively active patients.

Therapeutic Plasma Protein Comparison Embodiment

The example model generator 102, the PK server 108, and the drug dosing tool 110 were described in conjunction with determining a dosing regimen for one particular type of therapeutic plasma protein. However, in some examples, the model generator 102 may generate pharmacokinetic models for multiple types or brands of therapeutic plasma protein. This enables, for example, a user (e.g., a sales representative) to compare how the concentrations of the different therapeutic plasma proteins differ for the same patient for the same or different dosing intervals.

For example, a user may provide to the tool 110 patient information. The patient information is incorporated by the tool 110 into a first pharmacokinetic model for a first brand of therapeutic plasma protein and a second pharmacokinetic model for a second brand of therapeutic plasma protein. The user may then enter into the tool 110 a prescribed dosing regimen for the first therapeutic plasma protein and a prescribed dosing regimen for the second therapeutic plasma protein, which causes the tool 110 to display concurrently within a user interface a concentration of the first therapeutic plasma protein and the second therapeutic plasma protein over a time period for the patient. The example tool 110 may also enable the dosing intervals and/or doses to be modified (to the extent allowed or recommended by the manufacturer therapeutic plasma protein) to show how changes affect the concentration.

In particular, a user may use the tool 110 to show that the first brand of therapeutic plasma protein may be provided at three day dosing intervals with a dosage of 2600 IU while remaining above a target trough of 3% between doses. In comparison, the tool 110 shows the second brand of therapeutic plasma protein has to be provided every two days with a dosage of 2000 IU to remain above the same 3% target trough. In this instance, the first brand of the therapeutic plasma protein may be the better alternative to administer to a patient to reduce the number of infusions required per week while keeping the patient safe from bleeds.

Treatment Embodiment

As discussed above, the example drug dosing tool 110 and/or the PK server 108 determines an amount of therapeutic plasma protein (e.g., clotting factor VIII) to administer to a patient. To administer the therapeutic plasma protein to a patient, in one aspect, the therapeutic plasma protein includes one or more pharmaceutically acceptable carriers. The phrases "pharmaceutically" or "pharmacologically" acceptable refer to molecular entities and compositions that are stable, inhibit protein degradation such as aggregation and cleavage products, and in addition, do not produce allergic, or other adverse reactions when administered using routes well-known in the art. "Pharmaceutically acceptable carriers" include any and all clinically useful solvents, dispersion media, coatings, antibacterial and antifungal agents, isotonic and absorption delaying agents and the like.

The pharmaceutical formulations are administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Single or multiple administrations of the therapeutic plasma protein are carried out with the dose levels and pattern being selected by a healthcare provider. As discussed, the dosage regimen for the therapeutic plasma protein is based on various characteristics of the patient including age, gender, body weight, condition, activity level, diet, etc. The dosing regimen may also be based on a type of disease to be treated, the severity and course of the disease, whether the therapeutic plasma protein is administered for preventive or therapeutic purposes, previous therapy, a patient's clinical history and response to the therapeutic plasma protein, and the discretion of the healthcare provider. By way of example, a typical dose of a recombinant clotting factor FVIII therapeutic plasma protein is approximately 30 IU/kg to 50 IU/kg.

In one embodiment, a clotting factor FVIII therapeutic plasma protein may be administered by an initial bolus followed by a continuous infusion to maintain therapeutic circulating levels of the therapeutic plasma protein. In another embodiment, the inventive compound may be administered as a one-time dose. Those of ordinary skill in the art will readily optimize effective dosages and administration regimens as determined by good Tpractice and the clinical condition of the individual patient in conjunction with the results provided by the example tool 110. The frequency of dosing may depend on the pharmacokinetic parameters of the agents and the route of administration. The final dosage regimen is determined by the healthcare provider, considering various factors which modify the action of drugs, e.g. the drug's specific activity, the severity of the damage and the responsiveness of the patient, the age, condition, body weight, gender, and diet of the patient, the severity of any infection, time of administration and other clinical factors.

Preferably, an effective dose of the therapeutic plasma protein is 15-85 IU/kg (15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 62, 64, 65, 66, 67, 68, 69, 70, 71, 72, 73, 74, 75, 76, 77, 78, 79, 80, 81, 82, 83, 84, or 85 IU/kg) and the dosing interval is once every 1-5, 2-5, 3-5, 3-6, 3, 4, 5, 6, 7, or 8 or more days, or three times per week, or no more than three times per week. Additional therapeutic doses that may be used are about 10 to about 150 IU/kg, more specifically, about 100-110, 110-120, 120-130, 130-140, 140-150 IU/kg, and more specifically, about 110, 115, 120, 125, 130, 135, 140, 145, or 150 IU/kg. The dose should be high enough to experience efficacy, but not too high to avoid severe adverse effects. This therapeutic window is different for each patient, given environmental and genetic factors.

The relationship between patient and treatment-related variables including average Cmax, time below a target trough, and time spent above a specified threshold, for example, 5, 10, 20, 30% and 40% of a concentration of the therapeutic plasma protein within a patient, and risk for bleeding on prophylaxis are indices that may be used to optimize a dosing regimen. In this manner, individualized regimens with hemostatically-effective, non-hemophilic FVIII ranges and with increased prophylactic efficacy are created and implemented. In various embodiments, annual bleeding rates ("ABR") decrease by at least 50, 60, 70, 80, 81, 82, 83, 84, 85, 86, 87, 88, 89, 90, 91, 92, 93, 94, 95, 96, 97, 98 or 99% when, for example, a PK-guided dosing regimen as described above is followed as compared to on-demand dosing regimen.

Increasing time with a therapeutic plasma protein concentration below 1 IU dL(−1) is associated with increased total hemorrhages and hemarthroses in severe hemophilia A patients treated with regular prophylaxis regimens. Targeting trough levels at ≥1% above baseline using PK-guided dosing at 72 h intervals has been demonstrated to be an effective treatment strategy. While targeting FVIII trough at >1% above baseline is generally effective, this strategy alone may not be suitable for all patients, especially those with a recent history of high ABRs on on-demand therapy. Such patients may require alternative dosing regimens including higher doses and/or shorter dose intervals to achieve higher troughs and/or more frequent peaks of therapeutic plasma protein concentration.

In one embodiment, patients using a PK-guided dosing regimen experienced a median ABR of 2.0 (range 0-17.1) representing a 96% reduction in ABR from on-demand therapy. The individual FVIII therapeutic plasma protein half-lives (median: 11.7 hr; range: 7.3-30.7; IQR: 10.1-13.6; 5-95% percentiles: 7.7-21.4), and therefore, the FVIII therapeutic plasma protein dose/infusion (median 41.3 (IU/kg), range 18.9-84.9) varied widely in the study cohort. This enabled examination of the role of treatment- and patient-related variables other than FVIII therapeutic plasma protein troughs in achieving low ABRs in patients using individualized regimens.

Data from patients prescribed PK-guided dosing given every third day (n=34) were examined. Average Cmax for these patients was estimated using individual IVR values for each patient and their average dose per prophylactic infusion. The concentration of the therapeutic plasma protein and time spent above 5, 10, 20, 30, or 40% therapeutic plasma protein FVIII levels (i.e., within hemostatically effective, non-hemophilic range) in each patient were extrapolated using parameters from individual PK profiles and actual infusion records. A negative binomial multivariate regression model was used for analysis with age and BMI as covariates.

Figures 26, 27:
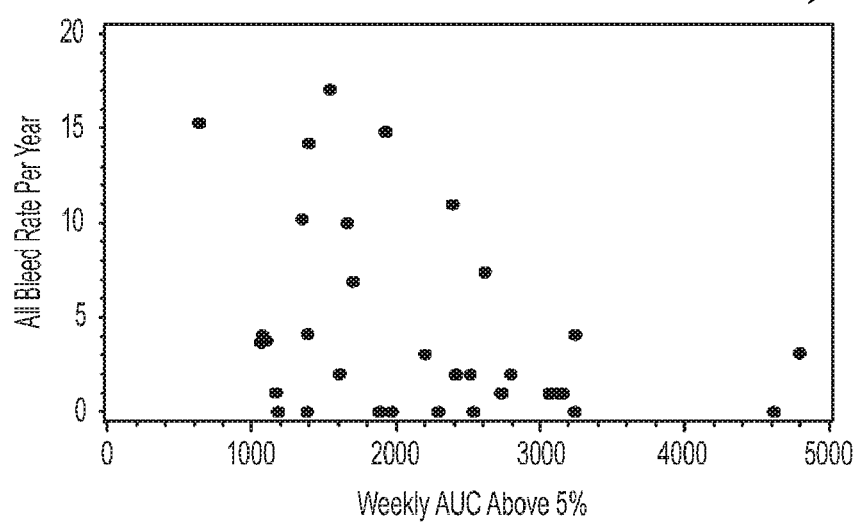

The estimate for average Cmax ranged from 24.3 to 167.5% (median 70.9%) in patients on PK-guided dosing with an every-three-day infusion schedule. As shown in graph 2300 of FIG. 23, a significant relationship between lower Cmax and increased risk for bleeding was seen. FIG. 24 includes a table 2400 that provides average Cmax and risk for bleeding. Time spent above a 20% concentration of the therapeutic plasma protein FVIII (joint bleeding only), time spent above a 30% concentration of the therapeutic plasma protein FVIII, and time spent above a 40% concentration of the therapeutic plasma protein showed a significant relationship with lower ABR. FIG. 25 shows a graph 2500 of a percent of total time spent above a 30% concentration of the therapeutic plasma protein FVIII in relation to bleeding risk. FIG. 26 shows a table 2600 of time spent in a non-hemophilic range in relation to a bleeding risk.

Similar significant relationships were found in all therapeutic plasma protein concentration variables tested (e.g., above 5%, 10%, and 20%). However, the co-efficient variable decreased with increasing average therapeutic plasma protein concentrations over the course of a week. FIG. 27 includes a diagram of a graph 2700 of average therapeutic plasma protein concentrations over the course of a week ("AUC") in relation to the bleed rate over the course of a year. FIG. 28 includes a table 2800 that shows average therapeutic plasma protein concentrations over the course of a week in relation to a risk for patient bleeding. As shown in FIG. 29, average Cmax, Time above % and weekly AUC variables were all strongly correlated.

Figure 30:
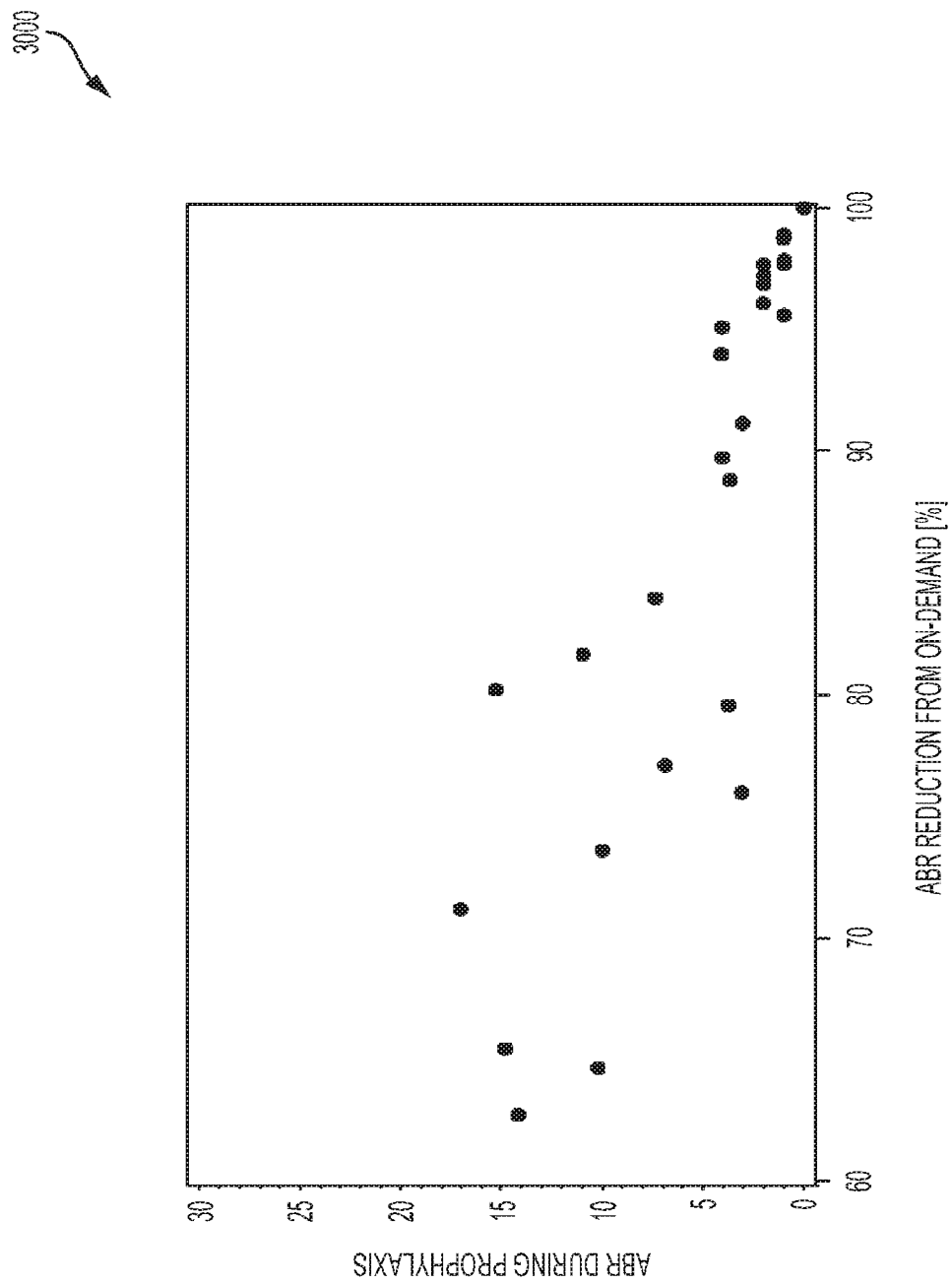

A substantial reduction in ABR during prophylaxis was seen in each patient. However many patients with higher ABR on prophylaxis appeared to have had more bleeding episodes during the preceding on-demand period and had a lower % ABR reduction on prophylaxis, as shown in graph 3000 of FIG. 30. These results demonstrate a relationship between higher Cmax values and/or time spent within "hemostatically effective", non-hemophilic FVIII range and better prophylactic efficacy in patients on PK-guided dosing given every third day. Conversely, increasing time spent within the lower FVIII therapeutic plasma protein range increased risk for bleeding. While targeting FVIII therapeutic plasma protein trough at >1% above baseline is generally effective and widely accepted in the scientific community, this strategy alone may not be suitable for all patients, especially those with a recent history of high ABRs on on-demand therapy. Such patients may require alternative dosing regimens including higher doses and/or shorter dose intervals to achieve higher troughs and/or more frequent peaks.

Processor

Figure 31:
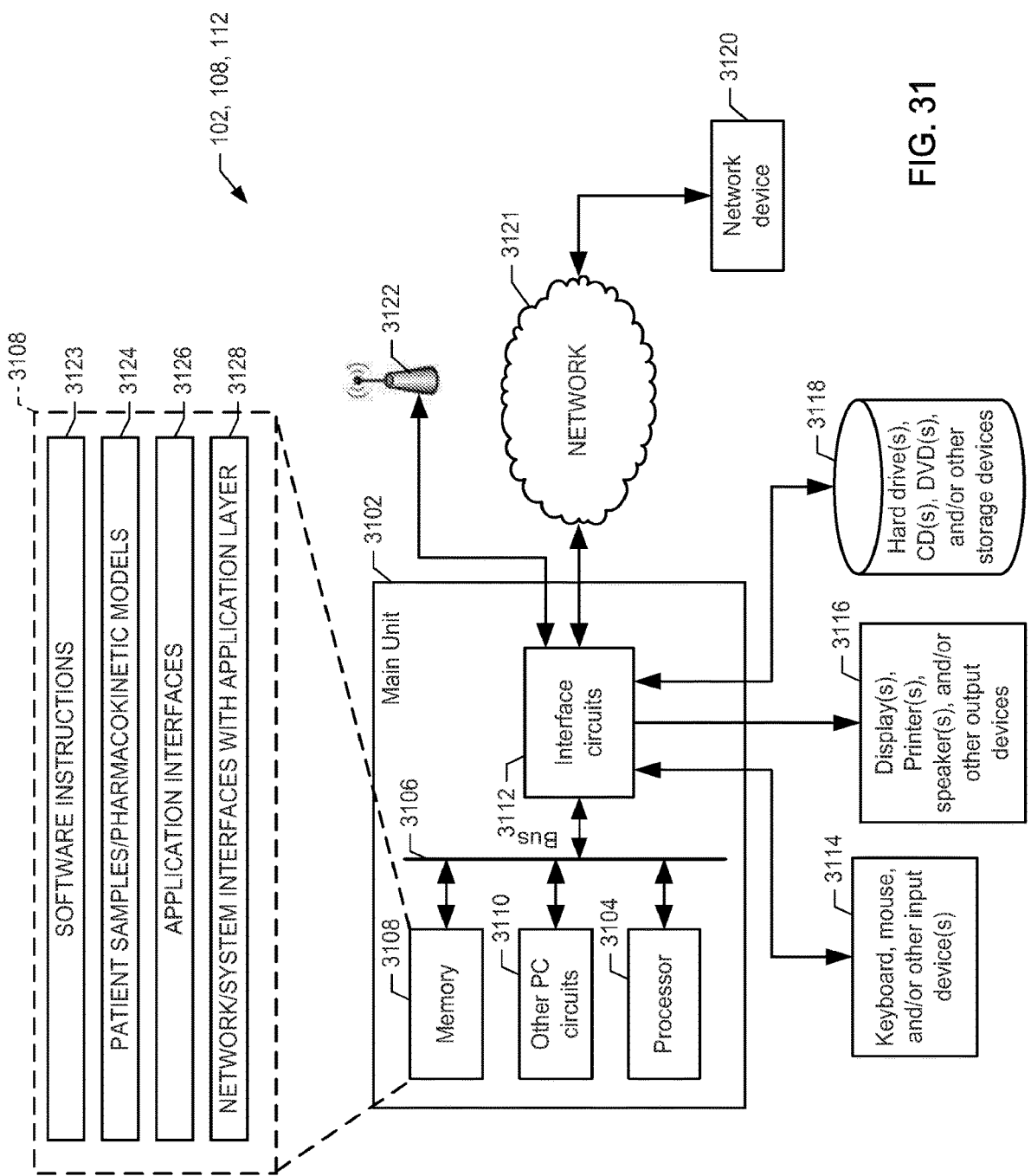
FIG. 31 shows a detailed block diagram of an example model generator, server, and/or client device of the pharmacokinetic drug dosing environment of FIG. 1, according to an example embodiment of the present disclosure.

A detailed block diagram of electrical systems of an example computing device (e.g., the model generator 102, PK server 108, and/or the client device 112) is illustrated in FIG. 31. In this example, the devices 102, 108, and/or 112 include a main unit 3102, which preferably includes one or more processors 3104 communicatively coupled by an address/data bus 3106 to one or more memory devices 3108, other computer circuitry 3110, and one or more interface circuits 3112. The processor 3104 may be any suitable processor, such as a microprocessor from the INTEL PENTIUM® or CORE™ family of microprocessors. The memory 3108 preferably includes volatile memory and non-volatile memory. Preferably, the memory 3108 stores a software program that interacts with the other devices in the environment 100, as described above. This program may be executed by the processor 3104 in any suitable manner. In an example embodiment, memory 3108 may be part of a "cloud" such that cloud computing may be utilized by devices 102, 108, and/or 112. The memory 3108 may also store digital data indicative of documents, files, programs, webpages, patient samples, pharmacokinetic models, patient pharmacokinetic profiles, etc. retrieved from (or loaded via) devices 102, 108, and/or 112.

The example memory devices 3108 store software instructions 3123, patient samples/pharmacokinetic models 3124, application interfaces 3126, user interface features, permissions, protocols, identification codes, content information, registration information, event information, and/or configurations. The memory devices 3108 also may store network or system interface features, permissions, protocols, configuration, and/or preference information 3128 for use by the devices 102, 108, and/or 112. It will be appreciated that many other data fields and records may be stored in the memory device 3108 to facilitate implementation of the methods and apparatus disclosed herein. In addition, it will be appreciated that any type of suitable data structure (e.g., a flat file data structure, a relational database, a tree data structure, etc.) may be used to facilitate implementation of the methods and apparatus disclosed herein.

The interface circuit 3112 may be implemented using any suitable interface standard, such as an Ethernet interface and/or a Universal Serial Bus (USB) interface. One or more input devices 3114 may be connected to the interface circuit 3112 for entering data and commands into the main unit 3102. For example, the input device 3114 may be a keyboard, mouse, touch screen, track pad, track ball, isopoint, image sensor, character recognition, barcode scanner, microphone, and/or a speech or voice recognition system.

One or more displays, printers, speakers, and/or other output devices 3116 may also be connected to the main unit 3102 via the interface circuit 3112. The display may be a cathode ray tube (CRTs), a liquid crystal display (LCD), or any other type of display. The display generates visual displays generated during operation of the device 102, 108, and/or 112. For example, the display may provide a user interface and may display one or more webpages received from the device 102, 108, and/or 112. A user interface may include prompts for human input from a user of the devices 102, 108, and/or 112 including links, buttons, tabs, checkboxes, thumbnails, text fields, drop down boxes, etc., and may provide various outputs in response to the user inputs, such as text, still images, videos, audio, and animations.

One or more storage devices 3118 may also be connected to the main unit 3102 via the interface circuit 3112. For example, a hard drive, CD drive, DVD drive, and/or other storage devices may be connected to the main unit 3102. The storage devices 3118 may store any type of data, such as identifiers, identification codes, registration information, patient samples, patient information, pharmacokinetic models, patient pharmacokinetic profiles, treatment regimens, statistical data, security data, etc., which may be used by the devices 102, 108, and/or 112.

The computing device 102, 108, and/or 112 may also exchange data with other network devices 3120 via a connection to a network 3121 (e.g., the Internet) or a wireless transceiver 3122 connected to the network 3121. Network devices 3120 may include one or more servers, which may be used to store certain types of data, and particularly large volumes of data which may be stored in one or more data repository. A server may process or manage any kind of data including databases, programs, files, libraries, identifiers, identification codes, registration information, content information, patient samples, patient information, treatment history related to clotting factor VIII, pharmacokinetic models, patient pharmacokinetic profiles, treatment regimens, statistical data, security data, etc. A server may store and operate various applications relating to receiving, transmitting, processing, and storing the large volumes of data. It should be appreciated that various configurations of one or more servers may be used to support, maintain, or implement the devices 102, 108, and/or 112 of the environment 100. For example, servers may be operated by various different entities, including operators of the PK server 108, hospital systems, patients, drug manufacturers, service providers, etc. Also, certain data may be stored in one of the devices 102, 108, and/or 112 which is also stored on a server, either temporarily or permanently, for example in memory 3108 or storage device 3118. The network connection may be any type of network connection, such as an Ethernet connection, digital subscriber line (DSL), telephone line, coaxial cable, wireless connection, etc.

Access to the devices 102, 108, and/or 112 can be controlled by appropriate security software or security measures. An individual third-party client or consumer's access can be defined by the device 102, 108, and/or 112 and limited to certain data and/or actions. Accordingly, users of the environment 100 may be required to register with one or more computing devices 102, 108, and/or 112.

Additional Patient Model Generation Embodiment

As discussed above in connection with FIGS. 1 and 2, the example model generator 102 is configured to determine or approximate a pharmacokinetic profile of a patient using a Bayesian model (e.g., the model described in Sheiner et al. Journal of Pharmaceutical Sciences 1982) of pharmacokinetic profiles (PK) of sampled patients (i.e., the Björkman population pharmacokinetic (PK) model developed from clinical trial data involving 152 study subjects ranging in age from 1 to 66 years old). The use of the Bayesian model enables fewer patient blood samples to be drawn to determine a pharmacokinetic profile of a patient. For instance, the Society of Thrombosis and Haemostasis ("ISTH") recommends that ten blood samples be collected from a patient over a 48 hour post-infusion of clotting factor VIII time period. However, the collection of ten samples over a 48 hour period is impractical and overly burdensome on patients and clinicians.

The example model generator 102 is configured to use as few as two patient samples in connection with the Bayesian model to determine or approximate a pharmacokinetic profile of a patient. Generally, the times of the sample collection relate to how the von Willebrand factor ("vWF") binds to clotting factor VIII during blood circulation. vWF is a blood glycoprotein that binds to other proteins including clotting factor VIII to help platelet adhesion (e.g., blood clotting) during bleeds. Unbound clotting factor VIII has a relatively short half-life of approximately 1 to 1.5 hours. vWF bound to clotting factor VIII (i.e., a vWF/FVIII complex) has a half-life of approximately 12 to 24 hours. Based on this information, relatively accurate patient models may be determined when a first sample is collected at approximately 1.5 to 4 hours after an infusion of clotting factor VIII, which corresponds to the half-life of unbound clotting factor VIII and a second sample is collected at 23 to 36 hours after the infusion, which corresponds to the half-life of the vWF/FVIII complex. More specifically, the first sample is collected at approximately 3 to 4 hours (+/−30 minutes) hours after an infusion of clotting factor VIII and the second sample is collected at 24 to 32 hours (+/−30 minutes) after the infusion.

Different patients have their own unique metabolism and disposition of clotting factor VIII. The example model generator 102 of FIG. 1 is configured to compare the two samples collected from the patient to the Björkman population model to determine patients with similar metabolism characteristics. The model generator 102 may select the population model from a plurality of population models stored in a database based on the patient's demographic profile (e.g., age, body weight, height, BMI, etc.). In this example, each population model can be associated with a particular set of demographic characteristics of a group of individuals such that the model generator 102 selects the population model associated with the demographic characteristics that match those of the patient. In another example, the model generator 102 may dynamically generate the population model by pulling stored patient sample data associated with those patient's having a similar demographic profile to that of the patient. The model generator 102 is configured to use these similarities in determining the pharmacokinetic profile of the patient (i.e., the demographic similarities between the patient and the individuals represented in the Björkman population model). The example model generator 102 is accordingly able to determine an optimal dosing regimen (e.g., dose and frequency) for different patients to maintain a therapeutically effective level of clotting factor VIII over a dosing interval in virtually any patient.

Figure 32:
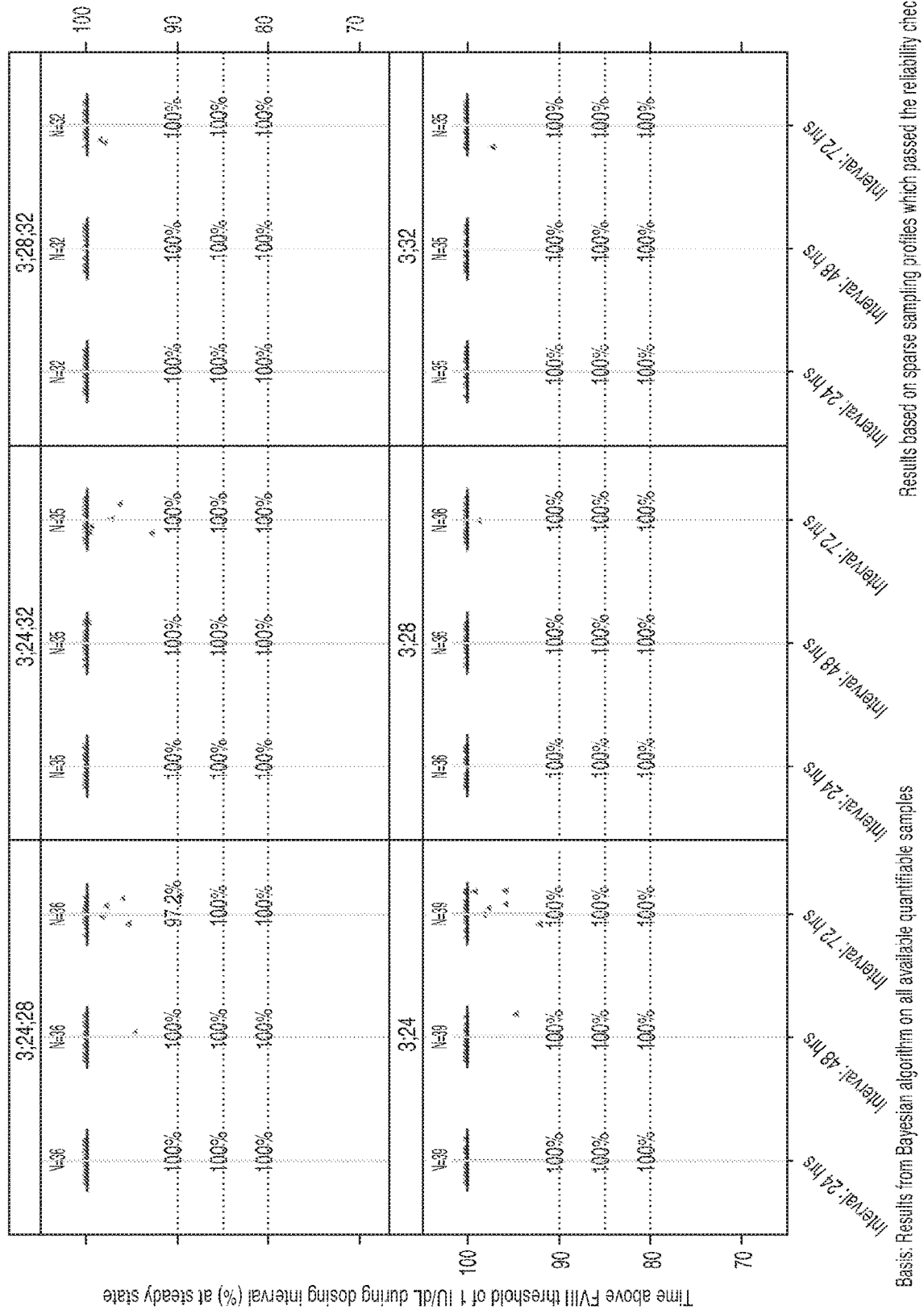
FIG. 32 shows a diagram of an amount of time in which clotting factor VIII was above a 1 IU/dL threshold for a sample of patients with longer half-lives.
Figure 33:
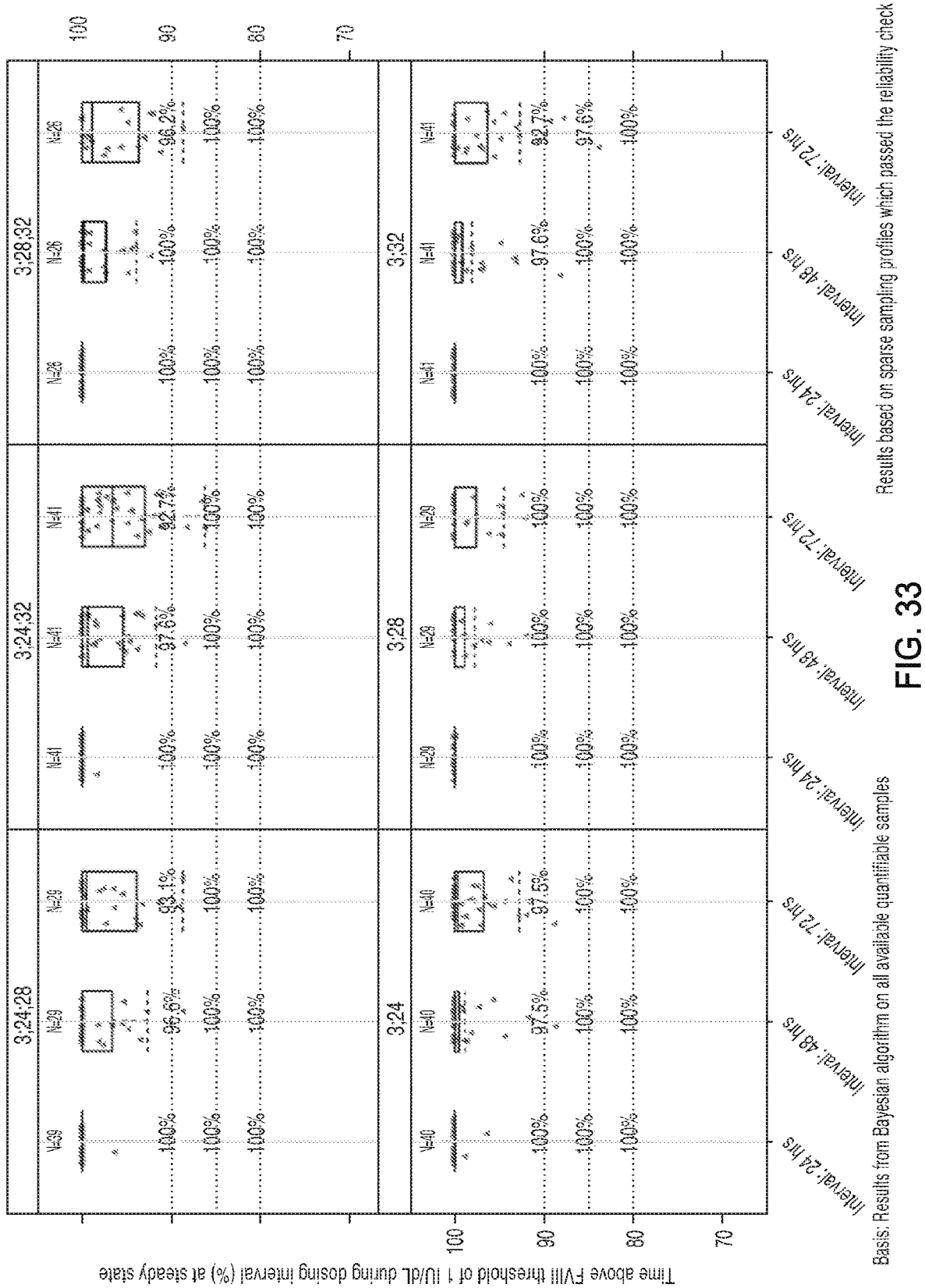
FIG. 33 shows a diagram of an amount of time in which clotting factor VIII was above a 1 IU/dL threshold for a sample of patients with shorter half-lives (i.e., half-lives less than 12 hours).

As discussed above, the risk of bleeding appears to increase dramatically when clotting factor VIII reaches low levels between infusions. Maintaining clotting factor VIII above 1 IU/dL, or higher significantly reduces the chances of a blood in a patient. However, the 1 IU/dL threshold varies from patient to patient and can be anywhere between 1-10 IU/dL as the therapeutically effective threshold for dosing as often as every 1 to 3 days. Notably, the 1 IU/dL threshold of a particular patient may significantly from those patients represented in the population model having similar demographic profiles as the particular patient. Specifically, those patients with shorter clotting factor VIII half-lives may have a higher bleed risk and may accordingly be dosed more frequently, and/or at higher dosing levels. For example, FIG. 32 shows a diagram of an amount of time in which clotting factor VIII was above a 1 IU/dL threshold for a sample of patients with longer half-lives. In comparison, FIG. 33 shows a diagram of an amount of time in which clotting factor VIII was above a 1 IU/dL threshold for patients with shorter half-lives (i.e., half-lives less than 12 hours). As illustrated in FIGS. 32 and 33, patients with longer half-lives have a very low risk of falling below the 1 IU/dL threshold while patients with shorter half-lives have comparably more risk of falling below the 1 IU/dL threshold. An appropriate dose amount and frequency is accordingly important in balancing convenience versus bleeding risk and should take into account a patient's clotting factor VIII half-life.

Examination has found that patients with a very low vWF, and hence a shorter half-life, often had PK parameters that were over-corrected by the model generator 102 towards the population mean. The over-correction was attributed to not placing enough weight (e.g., relative importance) on the individual patient's observed clotting factor VIII activity level. The over-correction meant that some patients with low vWF were recommended a lower dose than should have been prescribed, thereby exposing those patients to an increased risk of bleeding. However, vWF is not typically measured in routine clinical practice and therefore is not included in the population models. To account for vWF without directly measuring for vWF, the example model generator 102 is configured to account for the contribution of vWF and its pharmacokinetics using a pre-fit stage or evaluation to determine if more weight (e.g., relative importance) should be given to a patient's two or more samples and less weight (e.g., relative importance) to the population data. The use of the pre-fit stage or evaluation by the model generator 102 provides more accurate pharmacokinetic profile for a patient, thereby enabling an appropriate dose and frequency to be determined.

The pre-fit stage or evaluation performed by the example model generator 102 evaluates the disappearance, metabolism, or clearance of a patient's clotting factor VIII over time. A patient with low vWF will have less vWF/FVIII complex, leading to lower measured activity or metabolism. Increased clotting factor VIII clearance is associated with lower vWF levels, with an approximately linear relationship, until vWF measurements are about 100 to 120 IU/dL. Afterwards, there is no apparent impact of vWF on clotting factor FVIII clearance.

An example pre-fitting uses a non-compartmental approach (NCA) to fit the patient's sampled data. Specifically, it uses a log-linear regression of clotting factor VIII (FVIII) activity levels versus time. The activity levels versus time data can be for time points that are greater than or equal to a predetermined amount of time (e.g., 2.5 hours) after an infusion. The regression can be accomplished using an ordinary least square (OLS) regression. In other words, the model generator 102 generates a linear regression model with an intercept corresponding to a logarithmic function of the FVIII activity levels against an actual time point for patient samples. The time points correspond to those patient samples available after, e.g., 2.5 hours from an infusion (e.g., a PK infusion). The model generator 102 calculates an empirical estimate, $\lambda_z$, of the patient's FVIII elimination rate constant by obtaining an absolute value of a slope of the log-linear regression.

Additionally, the model generator 102 fits the patient sample data using the population Björkman model using a Bayes objective function. The model generator 102 denotes, as β, an estimated first-order rate constant for the FVIII elimination process (e.g., a population elimination rate constant of FVIII) defined by the fitting of the patient sample data to the population Björkman model.

The model generator then determines a relationship between the empirical estimate, $\lambda_z$, and the population elimination rate constant, β. In one aspect, the relationship is calculated at the ratio of the empirical estimate, $\lambda_z$, relative to the population elimination rate constant, β (e.g., relationship=$\lambda_z/\beta$). If the ratio is less than or equal to 1, the model generator 102 determines that sufficient weight (e.g., adequate relative importance) is being applied to the patient's sampled data relative to the population model. As such, the model generator 102 generates a PK profile of the patient using the standard population Björkman model. If the ratio is greater than 1, the model generator determines that insufficient weight (e.g., too low of a relative importance) is being applied to the patient's sample data relative to the population Björkman model. Accordingly, the model generator 102 increases the weight applied to the patients sampled data relative to the population Björkman model. This can occur by increasing a weight applied to the patient's sampled data relative to the population Björkman model, decreasing a weight applied to the population Björkman model relative to the patient's sampled data, or some combination of the two such that a relative weight applied to the patient sampled data is increased from a current weighting. In one particular example, the patient sampled data can be fit to the Björkman model via a Bayes objective function using an extra multiplicative constant in the term for clearance. This extra multiplicative constant can be the ratio defined by "$\lambda_z/\beta$".

Another example pre-fitting step uses a log-linear regression of measured clotting factor VIII clearance or activity versus time, using at least two well-selected samples, to yield an empirical estimate of $\lambda_z$. It should be noted that this $\lambda_z$ serves as a preliminary estimate and may only potentially be used by the model generator 102 to update the Bayesian model prior to generating the pharmacokinetic profile of the patient.

After the pre-fitting step, the example model generator 102 is configured to use the Bayesian algorithm or model to determine patient parameter estimates, as discussed above in connection with equations (1) to (4). The model generator 102 is configured to compare the empirical estimate of $\lambda_z$ from the individual patient to the Bayesian estimate of the elimination rate constant. If a ratio of the comparison is less than or equal to 1, the model generator 102 concludes the analysis by reporting the Bayesian fit estimates and determining the pharmacokinetic profile of the patient. However, if the ratio is greater than 1, the model generator 102 is configured to use the empirical estimate of $\lambda_z$ to temporarily update the Bayesian model and refit the patient's sample data to the population data.

Figure 34:
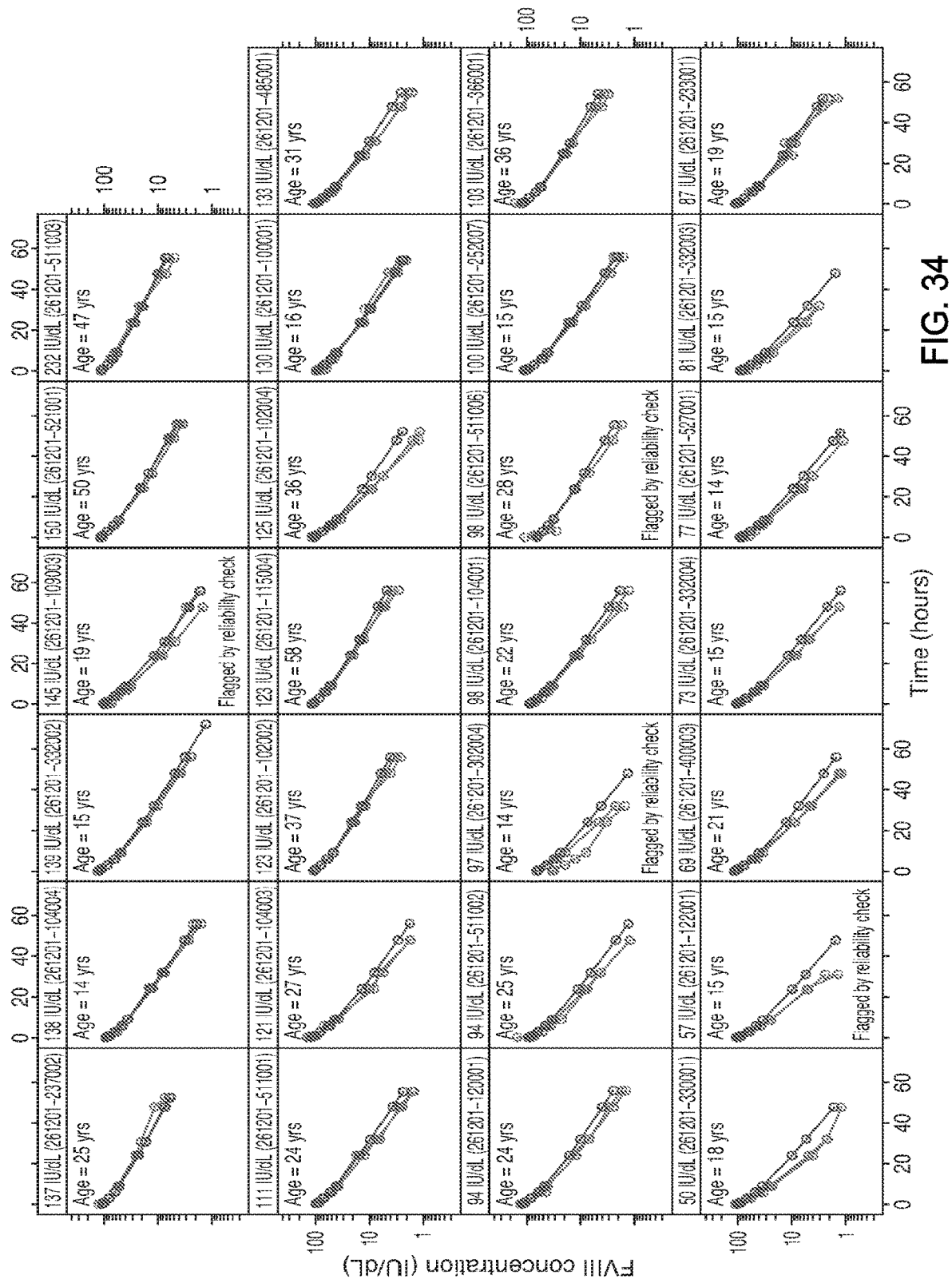
FIG. 34 shows a diagram of clotting factor FVIII clearance for 27 different patients over time.

FIG. 34 shows a diagram of clotting factor FVIII clearance for 27 different patients over time. It should be appreciated that pre-dose vWF levels were available for this data set. To estimate $\lambda_z$ (i.e., terminal or elimination phase rate constant) for each patient, the example model generator 102 is configured to determine a slope of the clotting factor FVIII clearance line at a terminal or elimination phase, which is typically after 24 hours. The slope of the line after terminal phase of clotting factor FVIII activity level corresponds to a rate constant. The model generator 102 then compares this empirical estimate of the rate constant to the Bayesian estimate of the elimination rate constant to determine if a ratio of the empirical estimate to the Bayesian estimate of the elimination rate constant is greater than or equal to 1. The model generator 102 is configured to use the empirical estimate of $\lambda_z$ to temporarily update the Bayesian model and refit the patient's sample data to the population data if the ratio is greater than 1. If not, the model generator 102 performs a Bayesian fir analysis to determine the pharmacokinetic profile of the patient.

Additionally or alternatively, the model generator 102 may use the patient sample data to determine a half-life for the patient. Patients with a half-life greater than 12 hours are not typically over-corrected. For these patients, the model generator 102 is configured to weight the population data more heavily than the patient's sample data. However, patients with a half-life less than 12 hours are typically over-corrected to the population mean. For these higher-risk patients, the model generator 102 is configured to weight the patient sample data more heavily than the population data. The weighting of patient sample data can be accomplished by using a variable (e.g., a weighting factor) that is assigned a numerical value. The numerical value enables the model generator 102 to determine a relative importance of the patient's sample data to that of the population data. As such, an absolute value of the numerical value can determine a level of weighting of the patient's sample data relative to the population data.

Figure 35:
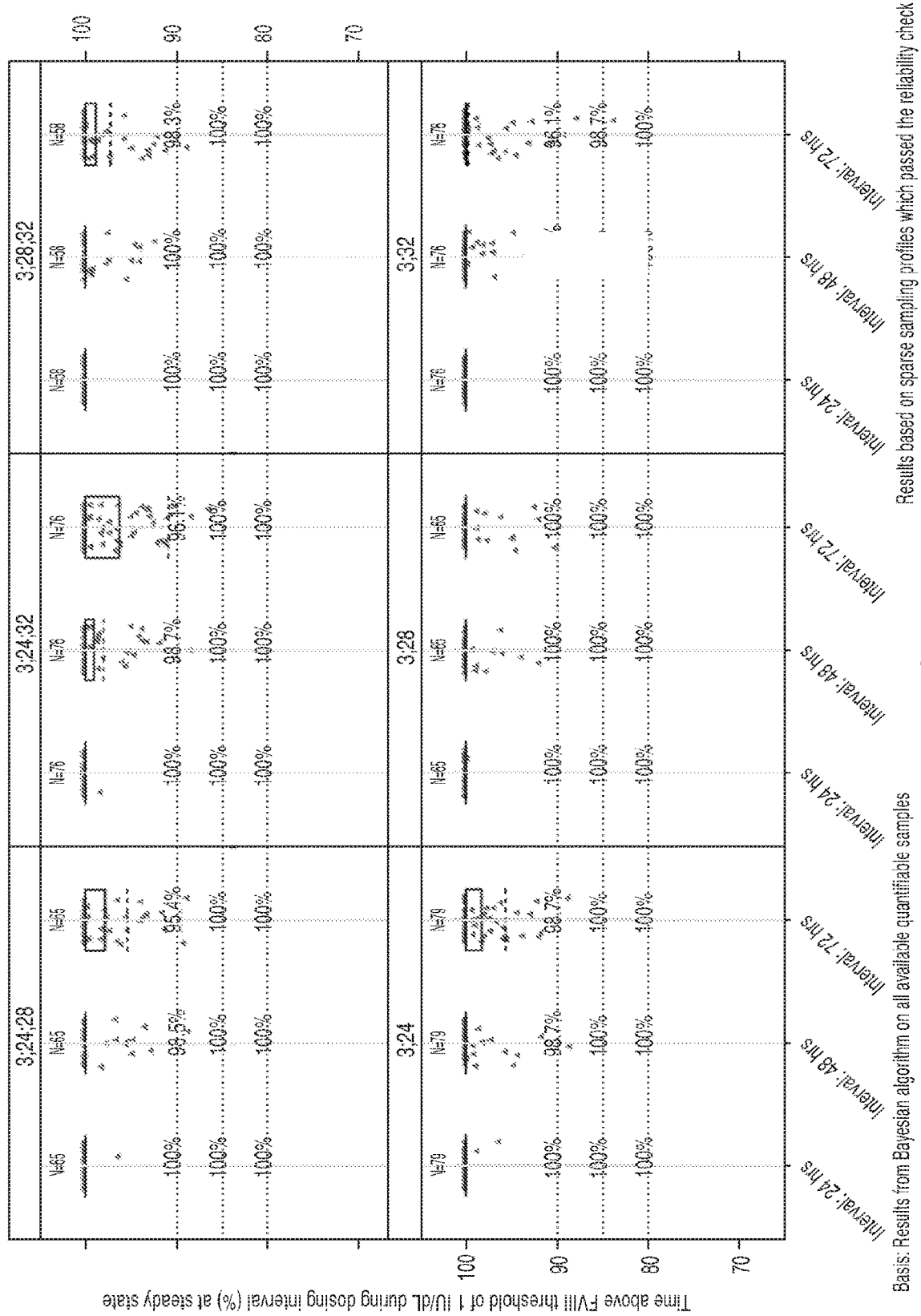
FIG. 35 shows a diagram of an amount of time in which clotting factor VIII was above a 1 IU/dL threshold for patients in which a pre-fitting step was used.

FIG. 35 shows a diagram of an amount of time in which clotting factor VIII was above a 1 IU/dL threshold for patients in which the pre-fitting step was used by the model generator 102. As illustrated in FIG. 35, the use of the pre-fitting step results in at least 90% or more of the patients to have at least 80% of their dosing intervals above the 1 IU/dL threshold regardless of the patient's clotting factor FVIII half-life. The use of the pre-fitting step accordingly accounts for any over-correction for patients with low levels of vWF.

It should be appreciated that in other embodiments, the vWF levels may be measured by performing a blood draw prior to administering clotting factor FVIII. Further, activity of vFW and clotting factor FVIII may be determined from blood samples drawn after the infusion. Together, these measurements may provide a vWF clearance over time, which may be used by the model generator 102 to update and/or refine the Bayesian model and/or refine the pharmacokinetic profile of a patient. For example, the Bayesian model may account for vWF as a covariate related to the clearance of clotting factor FVIII to provide guidance for FVIII dosage amount, for a given dosing frequency and target maintenance activity threshold.

It will be appreciated that all of the disclosed methods and procedures described herein can be implemented using one or more computer programs or components. These components may be provided as a series of computer instructions on any conventional computer-readable medium, including RAM, ROM, flash memory, magnetic or optical disks, optical memory, or other storage media. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. An apparatus comprising:
a processor;
a non-transitory storage medium comprising memory storing instructions that are configured, when executed by the processor, to cause the apparatus to perform a procedure comprising:
determining, via the processor, an estimated pharmacokinetic profile of a patient using a Bayesian model of pharmacokinetic profiles of sampled patients, the estimated pharmacokinetic profile based upon at least one of a body weight or an age of the patient;
determining, via the processor, a first dosing regimen for a first specified dosing interval including (i) a first dosage and (ii) a first therapeutic plasma protein level in the patient varying over time based at least upon the estimated pharmacokinetic profile;
determining, via the processor, a second dosing regimen for a second specified dosing interval including (i) a second dosage and (ii) a second therapeutic plasma protein level in the patient varying over time based at least upon the estimated pharmacokinetic profile and in response to receiving a change to at least one of a minimum therapeutic plasma protein level, dosage interval, or dosage of the therapeutic plasma protein, wherein the change to the at least one of the minimum therapeutic plasma protein level, the dosage interval, or the dosage is received via a graphical user interface (GUI) associated with the apparatus that includes fields for user input for adjusting at least one of the minimum therapeutic plasma protein level, the dosage interval, or the dosage;
displaying the second dosing regimen on a client device and within the GUI;
adjusting, via the processor, the estimated pharmacokinetic profile of the patient upon previous treatments of the patient; and
determining, via the processor, if the patient has a therapeutic plasma protein half-life greater than a predetermined threshold, wherein:
a first weighting factor is applied to the Bayesian model of pharmacokinetic profiles of sampled patients if the half-life of the patient is greater than the predetermined threshold, and
a second weighting factor, less than the first weighting factor, is applied to the Bayesian model of pharmacokinetic profiles of sampled patients if the half-life of the patient is less than the predetermined threshold.

2. The apparatus of claim 1, wherein the second specified dosing interval is longer than the first specified dosing interval.

3. The apparatus of claim 2, wherein the first specified dosing interval is 48 hours and the second specified dosing interval is 72 hours.

4. The apparatus of claim 1, wherein the first dosage is determined such that the first therapeutic plasma protein level in the patient does not fall below an initial minimum concentration threshold, and wherein the initial minimum concentration threshold is less than 20% relative to baseline plasma protein level for the patient.

5. The apparatus of claim 1, wherein the first therapeutic plasma protein level in the patient is based upon at least one of an initial minimum concentration threshold, the first dosage, or the first specified dosing interval, and the second therapeutic plasma protein level in the patient is based upon at least one of the initial minimum concentration threshold, the first dosage, or the first specified dosing interval.

6. The apparatus of claim 1, wherein the Bayesian model includes a two-compartment model having a first compartment corresponding to a time to metabolize the therapeutic plasma protein and a second compartment corresponding to a dose for achieving a certain amount of the therapeutic plasma protein within the patient.

7. The apparatus of claim 1, wherein the minimum therapeutic plasma protein level is a first minimum protein level, and wherein the instructions, when executed by the processor, cause the apparatus to perform the procedure comprising:

receiving, at the processor, a selection of a second minimum protein level greater that the first minimum protein level;

determining, via the processor, a duration of time the second therapeutic plasma protein level in the patient is below the second minimum protein level; and displaying, in the GUI, a graphical representation of the duration of time in conjunction with the display of the second dosing regimen.

8. The apparatus of claim 7, wherein the duration of time is further based on the time the second therapeutic plasma protein level is above the first minimum protein level.

9. The apparatus of claim 1, wherein the estimated pharmacokinetic profile is based at least on two blood samples collected from the patient after an infusion of therapeutic plasma protein.

* * * * *

UNITED STATES PATENT AND TRADEMARK OFFICE
CERTIFICATE OF CORRECTION

PATENT NO. : 11,081,211 B2
APPLICATION NO. : 17/070599
DATED : August 3, 2021
INVENTOR(S) : Kuchimanchi et al.

Page 1 of 1

It is certified that error appears in the above-identified patent and that said Letters Patent is hereby corrected as shown below:

On the Title Page

Item (73), Replace "BAXALTA INCORPORATED, Bannockburn, IL (US); BAXALTA GMBH, Glattpark (CH)" with the following Assignee: "TAKEDA PHARMACEUTICAL COMPANY LIMITED, Osaka (JP)."

Signed and Sealed this
Tenth Day of May, 2022

Katherine Kelly Vidal
*Director of the United States Patent and Trademark Office*